(12) United States Patent
Aida et al.

(10) Patent No.: US 9,975,826 B2
(45) Date of Patent: May 22, 2018

(54) PRODUCTION METHOD OF ALIPHATIC ALCOHOL

(71) Applicant: KAO CORPORATION, Tokyo (JP)

(72) Inventors: Sho Aida, Tokyo (JP); Taichi Homma, Haga-gun (JP)

(73) Assignee: KAO CORPORATION, Tokyo (JP)

( * ) Notice: Subject to any disclaimer, the term of this patent is extended or adjusted under 35 U.S.C. 154(b) by 0 days. days.

(21) Appl. No.: 15/510,846

(22) PCT Filed: Nov. 17, 2015

(86) PCT No.: PCT/JP2015/082812
§ 371 (c)(1),
(2) Date: Mar. 13, 2017

(87) PCT Pub. No.: WO2016/080552
PCT Pub. Date: May 26, 2016

(65) Prior Publication Data
US 2017/0275221 A1    Sep. 28, 2017

(30) Foreign Application Priority Data

Nov. 20, 2014 (JP) ................................. 2014-235266

(51) Int. Cl.
| | | |
|---|---|---|
| *C07C 29/141* | (2006.01) | |
| *B01J 23/00* | (2006.01) | |
| *B01J 35/10* | (2006.01) | |
| *B01J 23/75* | (2006.01) | |
| *B01J 23/72* | (2006.01) | |

(52) U.S. Cl.
CPC ............. *C07C 29/141* (2013.01); *B01J 23/72* (2013.01); *B01J 23/75* (2013.01); *B01J 35/1033* (2013.01); *B01J 35/1052* (2013.01)

(58) Field of Classification Search
CPC .......... C07C 29/141; B01J 23/72; B01J 23/75
See application file for complete search history.

(56) References Cited

U.S. PATENT DOCUMENTS

| | | | |
|---|---|---|---|
| 5,386,066 A | 1/1995 | Schneider et al. | |
| 5,481,048 A | 1/1996 | Tsukada et al. | |
| 7,459,571 B2 * | 12/2008 | Schlitter ................. | B01J 23/72 |
| | | | 549/295 |
| 2003/0187309 A1 | 10/2003 | Prinz et al. | |

FOREIGN PATENT DOCUMENTS

| | | |
|---|---|---|
| EP | 0 656 366 A1 | 6/1995 |
| EP | 0656336 A1 | 6/1995 |
| JP | 48-62708 A | 9/1973 |
| JP | 61-5036 A | 1/1986 |
| JP | 7-163880 A | 6/1995 |
| JP | 8-169855 A | 7/1996 |
| JP | 2009-255047 A | 11/2009 |
| WO | 92/20447 A1 | 11/1992 |
| WO | 97/34694 A1 | 9/1997 |
| WO | 2013/086453 A1 | 6/2013 |

OTHER PUBLICATIONS

International Search Report for PCT/JP2015/082812 dated Feb. 29, 2016.
Written Opinion of the International Searching Authority for PCT/JP2015/082812 dated Feb. 29, 2016.

* cited by examiner

*Primary Examiner* — Sikarl A Witherspoon
(74) *Attorney, Agent, or Firm* — Birch, Stewart, Kolasch & Birch, LLP

(57) ABSTRACT

Provided is a method for producing an aliphatic alcohol having 8 or more and 22 or less carbon atoms through hydrogenation of a fatty acid or a fatty acid ester using a catalyst,
wherein the catalyst carries a catalyst metal on a support,
(a) the catalyst contains one or more elements selected from Co and Cu as the catalyst metal, (b) the total pore volume of the catalyst is 0.05 mL/g or more, and (c) the volume of pores with a pore size of 0.1 μm or more and 500 μm or less is 50% or more of the total pore volume of the catalyst.

19 Claims, No Drawings

PRODUCTION METHOD OF ALIPHATIC ALCOHOL

FIELD OF THE INVENTION

The present invention relates to a method for producing an aliphatic alcohol through hydrogenation of a fatty acid or a fatty acid ester. Specifically, the present invention relates to a highly productive method for producing a high-quality aliphatic alcohol having 8 or more and 22 or less carbon atoms in which the hydrogenation of a fatty acid or a fatty acid ester is conducted using a catalyst having a specific structure and in which the reaction selectivity has been improved significantly.

BACKGROUND OF THE INVENTION

As a method for producing an alcohol, a method of conducting catalytic hydrogenation of a fatty acid or a fatty acid ester is generally known. With respect to the catalysts used for the hydrogenation of fatty acids or fatty acid esters, studies on many metal catalysts such as noble metal catalysts including Pt and Pd, Cu, Ni and Co, which are base metal catalysts, have been reported. Copper-based catalysts have been mainly proposed as the catalysts used for the hydrogenation of fatty acid esters, and for example copper-chromium catalysts are industrially used. For example, JP-A-7-163880 describes that such catalysts are reduced in a liquid phase under a certain condition and used for hydrogenation. Moreover, attempts have been made for a long time to obtain an alcohol through catalytic hydrogenation of a free carboxylic acid using a catalyst.

For example, JP-A-61-5036 discloses a method for producing an alcohol using a Co catalyst containing a metal selected from Al, Zr, Mo, Y and the like and a metal selected from Cu, Pt, Pd and the like. Moreover, JP-A-48-62708 discloses a method for producing an alcohol using a Co catalyst combined with Fe, Zn, P or the like. JP-A-7-163880, JP-A-61-5036 and JP-A-48-62708 describe that a prepared catalyst is molded for example by shaping into pellets and calcining and then used.

JP-A-8-169855 discloses a method for producing a higher alcohol in which a tiny amount of a basic material is added to an oil or a fatty acid ester to prevent the generation of dialkyl ethers, alkyl methyl ethers and hydrocarbons as by-products during the hydrogenation of the oil or the fatty acid ester. JP-A-2009-255047 discloses a honeycomb structure which is formed by integral molding of a honeycomb member used for treating exhaust gas from an internal-combustion engine and inorganic fibers. The pores of 0.005 to 0.03 μm in the honeycomb structure mainly contribute to the removal of chemically harmful substances, and the pores with a pore size of 1 to 50 μm reduce the pressure loss and increase the collection efficiency of PM (fine particulate matters).

SUMMARY OF THE INVENTION

As a method for producing a higher alcohol, a method in which a fatty acid or a fatty acid ester is hydrogenated in the presence of a hydrogenation catalyst at a high temperature at high pressure is known, as described for example in the above-described JP-A-7-163880, JP-A-61-5036 and JP-A-48-62708. It is known that, in the production method, the reaction progresses excessively on the catalyst during the hydrogenation and a part of the obtained higher alcohol is dehydrated, resulting in the generation of high amounts of dialkyl ethers, alkyl methyl ethers and hydrocarbons as by-products. As a result, there are problems because the yield of the alcohol to be obtained decreases and because the quality deteriorates due to the decrease in the purity. On the other hand, when the production method described in JP-A-8-169855 is used in order to avoid the problems, then there are problems in that the increase in the production costs is unavoidable due to the post-treatment of the basic substance added.

With respect to the honeycomb structure described in JP-A-2009-255047, pores that contribute to the removal of chemically harmful substances are those with a pore diameter of 0.005 to 0.03 μm. It is merely disclosed that pores with a pore diameter of 1 to 15 μm and those with a pore diameter of 15 to 50 μm are capable of keeping the pressure loss low and increasing the collection efficiency of PM, but the diffusion of reaction products from the interior of the catalyst and the prevention of the generation of by-products are not disclosed at all. Moreover, production of an alcohol is not described, either.

An objective of the present invention is to provide a highly productive method for producing a high-quality aliphatic alcohol which prevents the generation of by-products such as hydrocarbons during the hydrogenation of a fatty acid or a fatty acid ester, which does not require special post-treatment and which is industrially satisfactory.

The present invention relates to a method for producing an aliphatic alcohol having 8 or more and 22 or less carbon atoms through hydrogenation of a fatty acid or a fatty acid ester using a catalyst, wherein the catalyst contains a catalyst metal carried on a support, (a) the catalyst contains one or more elements selected from Co and Cu as the catalyst metal, (b) the total pore volume of the catalyst is 0.05 mL/g or more, and (c) the volume of pores with a pore size of 0.1 μm or more and 500 μm or less is 50% or more of the total pore volume of the catalyst.

The catalyst used in the production method of the present invention has high reaction selectivity and is industrially satisfactory. When the production method of the present invention is used, an aliphatic alcohol having 8 or more and 22 or less carbon atoms can be produced in a high yield from a fatty acid or a fatty acid ester as the raw material, and it is very advantageous from the industrial point of view.

It is not clear why the amounts of by-products are reduced and the reaction selectivity improves when a catalyst with a specific pore structure which meets the conditions of the present invention is used, but it is believed as follows. That is, in the conventional techniques, from the viewpoints of molding strength and molding properties, catalysts with pores smaller than those of the catalyst used in the present invention, such as tablet-compressed catalysts and extrusion molded catalysts, have been used. However, the pore sizes of the conventional catalysts are insufficient from the viewpoint of improving the diffusion of reaction products. On the other hand, by using a catalyst with a specific pore structure of a size which is by far larger than those of the conventional techniques, as in the present invention, the diffusion of reaction products in the pores of the catalyst is promoted, and the reaction products rapidly flow out of the interior of the pores. It is believed that, as a result, the retention time of the products in the interior of the pores can be shortened as compared to the conventional catalysts, and the excessive reaction during the retention in the interior of the catalyst pores is prevented, resulting in the decrease in the amounts of by-products.

DESCRIPTION OF EMBODIMENTS

<Fatty Acid or Fatty Acid Ester>

As the raw material used in the production method of the present invention, from the viewpoints of reactivity and selectivity, a fatty acid or a fatty acid ester is used.

As the fatty acid, synthetic fatty acids are mentioned in addition to animal- and plant-derived natural fatty acids obtained from an animal fat such as beef tallow and fish oil or a vegetable oil such as palm kernel oil, coconut oil, palm oil, soybean oil and rape oil. From the viewpoint of usability of reaction products as surfactants, and from the viewpoint of availability of raw materials, the fatty acid is preferably derived from a vegetable oil, more preferably derived from one or more kinds of oils selected from palm kernel oil, coconut oil and palm oil, and further preferably derived from palm kernel oil or coconut oil. From the same viewpoint, the carbon number of the fatty acid is preferably eight or more, and preferably 22 or less, and more preferably 18 or less. Moreover, from the same viewpoint, the fatty acid preferably has a linear or branched, saturated or unsaturated hydrocarbon group, more preferably has a linear, saturated or unsaturated hydrocarbon group and further preferably has a linear, saturated hydrocarbon group.

The fatty acid ester is a fatty acid alcohol ester which is an ester of a fatty acid and a monohydric alcohol having 1 or more and 22 or less carbon atoms, an oil or the like. The oil is an animal fat such as beef tallow and a fish oil or a vegetable oil such as palm kernel oil, coconut oil, palm oil, soybean oil and rape oil. Among them, from the viewpoint of usability of reaction products as surfactants, an oil derived from a vegetable oil is preferable, an oil derived from one or more kinds of oil selected from palm kernel oil, coconut oil and palm oil is more preferable, and an oil derived from palm kernel oil or coconut oil is further preferable. From the same viewpoint, the carbon number of the constituent fatty acid of the oil is preferably eight or more, and preferably 22 or less, and more preferably 18 or less.

The fatty acid alcohol ester can be obtained through transesterification of glycerides in the oil and a monohydric alcohol having 1 or more and 22 or less carbon atoms or through esterification of a fatty acid obtained through hydrolysis of the oil and a monohydric alcohol having 1 or more and 22 or less carbon atoms. From the viewpoint of usability of reaction products as surfactants, and from the viewpoint of availability of raw materials, the constituent fatty acid of the fatty acid alcohol ester is preferably a fatty acid derived from vegetable oil, more preferably a fatty acid derived from one or more kinds of oil selected from palm kernel oil, coconut oil and palm oil, and further preferably a fatty acid derived from palm kernel oil or coconut oil. From the same viewpoint, the carbon number of the constituent fatty acid is preferably eight or more, and preferably 22 or less, and more preferably 18 or less. Moreover, from the same viewpoint, the constituent fatty acid preferably has a linear or branched, saturated or unsaturated hydrocarbon group, more preferably has a linear, saturated or unsaturated hydrocarbon group and further preferably has a linear, saturated hydrocarbon group.

From the viewpoint of improving the productivity, the monohydric alcohol having 1 or more and 22 or less carbon atoms is preferably a lower monohydric alcohol having one or more and four or less carbon atoms, more preferably methanol or ethanol, and further preferably methanol.

The transesterification and the esterification can be conducted by known methods. Any of continuous, batch and semi-batch reaction processes can be used for the reaction, but when a large amount of ester is produced, a continuous process is advantageous. The catalyst for the transesterification is a homogeneous alkali catalyst such as sodium hydroxide, potassium hydroxide and sodium alcoholate or a solid catalyst such as an ion exchange resin, hydrous zirconium oxide, aluminum phosphate, sulfuric acid-on-zirconia and titanosilicate.

When the transesterification of the oil is conducted using a homogeneous alkali catalyst, from the viewpoint of reducing the amount of by-products, the fatty acid contained in the oil is converted to an ester with a monohydric alcohol having 1 or more and 22 or less carbon atoms preferably using an acid catalyst such as sulfuric acid and para-toluenesulfonic acid before the transesterification. The reaction temperature of the transesterification of the oil using a homogeneous alkali catalyst is, from the viewpoint of reactivity, preferably 30° C. or higher, and more preferably 40° C. or higher and, from the viewpoint of the yield of the fatty acid alcohol ester, preferably 90° C. or lower, and preferably 80° C. or lower. The reaction pressure of the transesterification of the oil using a homogeneous alkali catalyst as gauge pressure is, from the viewpoint of reactivity, preferably atmospheric pressure or higher and 0.5 MPa or lower, and more preferably atmospheric pressure.

The amount by mole of the monohydric alcohol having 1 or more and 22 or less carbon atoms used for the transesterification is, based on the moles of the glycerides in the oil, from the viewpoint of reactivity, preferably 1.5 times or more, more preferably three times or more, and further preferably six times or more and, from the economic viewpoint, preferably 15 times or less, and more preferably 12 times or less.

As the fatty acid or the fatty acid ester, it is generally preferable to use a fatty acid or a fatty acid ester from which sulfur components have been reduced or removed through desulfurization in the presence of a catalyst or desulfurization such as distillation or adsorption.

<Catalyst>

The catalyst used in the present invention contains a catalyst metal carried on a support and contains one or more elements selected from Co and Cu as the catalyst metal. The total pore volume of the catalyst is 0.05 mL/g or more, and the volume of pores with a pore size of 0.1 μm or more and 500 μm or less is 50% or more of the total pore volume of the catalyst. In the following description, the catalyst metal means an element which constitutes a substance in the catalyst which hydrogenates a fatty acid or a fatty acid ester in a hydrogen atmosphere. Moreover, a compound containing the catalyst metal is called a catalyst metal compound.

The total pore volume of the catalyst used in the present invention is, from the viewpoints of improving the diffusion of raw reaction materials into the interior of the catalyst and the diffusion of reaction products from the interior of the catalyst, and thereby improving the selectivity, 0.05 mL/g or more and, from the viewpoints of improving the efficiency of contact between the catalyst metal and raw reaction materials in the interior of the catalyst, and thereby improving the catalytic activity, and from the viewpoint of improving the strength of the catalyst, preferably 10 mL/g or less, more preferably 4 mL/g or less, and further preferably 2.5 mL/g or less.

Moreover, the total pore volume of the catalyst is, from the viewpoints of improving the diffusion of raw reaction materials into the interior of the catalyst and the diffusion of reaction products from the interior of the catalyst, and thereby improving the selectivity, when an alcohol is produced from a fatty acid or oil, preferably 0.15 mL/g or more, more preferably 0.5 mL/g or more, and further preferably 0.6 mL/g or more and, from the viewpoints of improving the efficiency of contact between the catalyst metal and raw reaction materials in the interior of the catalyst, and thereby improving the catalytic activity, and from the viewpoint of improving the strength of the catalyst, furthermore preferably 1.6 mL/g or less, and furthermore preferably 1 mL/g or less.

Moreover, the total pore volume of the catalyst is, from the viewpoints of improving the diffusion of raw reaction materials into the interior of the catalyst and the diffusion of reaction products from the interior of the catalyst, and thereby improving the selectivity, when an alcohol is produced from an ester obtained from a fatty acid and a monohydric alcohol, preferably 1.2 mL/g or more, and more preferably 1.8 mL/g or more and, from the viewpoints of improving the efficiency of contact between the catalyst metal and raw reaction materials in the interior of the catalyst, and thereby improving the catalytic activity, and from the viewpoint of improving the strength of the catalyst, further preferably 2 mL/g or less, and furthermore preferably 1.9 mL/g or less.

In this regard, the catalytic activity here means the rate of the hydrogenation for producing a corresponding alcohol from a fatty acid or a fatty acid ester in the presence of the catalyst used in the present invention and specifically is the decrease rate of the fatty acid content or the fatty acid ester content in the raw materials. Moreover, the selectivity means the production amount of hydrocarbons in the hydrogenation of the present invention and specifically is the hydrocarbon content in the reaction solution at a certain point.

The volume of pores with a pore size of 0.1 $\mu$m or more and 500 $\mu$m or less in the catalyst used in the present invention is, from the viewpoints of improving the diffusion of raw reaction materials into the interior of the catalyst and the diffusion of reaction products from the interior of the catalyst, and thereby improving the selectivity and the catalytic activity, 50% or more of the total pore volume and, from the viewpoints of improving the efficiency of contact between the catalyst metal and raw reaction materials in the interior of the catalyst, and thereby improving the catalytic activity, preferably 100% or less of the total pore volume.

Moreover, the volume of pores with a pore size of 0.1 $\mu$m or more and 500 $\mu$m or less in the catalyst is, from the viewpoints of improving the diffusion of raw reaction materials into the interior of the catalyst and the diffusion of reaction products from the interior of the catalyst, and thereby improving the selectivity and the catalytic activity, when an alcohol is produced from a fatty acid or oil, preferably 55% or more, more preferably 60% or more, and further preferably 63% or more and, from the viewpoints of improving the efficiency of contact between the catalyst metal and raw reaction materials in the interior of the catalyst, and thereby improving the catalytic activity, preferably 95% or less, more preferably 90% or less, further preferably 85% or less, and furthermore preferably 84% or less.

Moreover, the volume of pores with a pore size of 0.1 $\mu$m or more and 500 $\mu$m or less in the catalyst is, from the viewpoints of improving the diffusion of raw reaction materials into the interior of the catalyst and the diffusion of reaction products from the interior of the catalyst, and thereby improving the selectivity and the catalytic activity, when an alcohol is produced from an ester obtained from a fatty acid and a monohydric alcohol, further preferably 70% or more, furthermore preferably 80% or more, furthermore preferably 90% or more, and furthermore preferably 95% or more and, from the viewpoints of improving the efficiency of contact between the catalyst metal and raw reaction materials in the interior of the catalyst, and thereby improving the catalytic activity, preferably 97% or less, and more preferably 96% or less.

The mode of the pore size of the catalyst used in the present invention is, from the viewpoints of improving the diffusion of raw reaction materials into the interior of the catalyst and the diffusion of reaction products from the interior of the catalyst, and thereby improving the selectivity and the catalytic activity, preferably 0.035 $\mu$m or more, and more preferably 0.1 $\mu$m or more and, from the viewpoints of improving the efficiency of contact between the catalyst metal and raw reaction materials in the interior of the catalyst, and thereby improving the catalytic activity, and from the viewpoint of improving the strength of the catalyst, preferably 100 $\mu$m or less.

Moreover, the mode of the pore size of the catalyst is, from the viewpoints of improving the diffusion of raw reaction materials into the interior of the catalyst and the diffusion of reaction products from the interior of the catalyst, and thereby improving the selectivity and the catalytic activity, when an alcohol is produced from a fatty acid or oil, further preferably 15 $\mu$m or more, furthermore preferably 40 $\mu$m or more, furthermore preferably 50 $\mu$m or more, furthermore preferably 55 $\mu$m or more, and furthermore preferably 56 $\mu$m or more and, from the viewpoints of improving the efficiency of contact between the catalyst metal and raw reaction materials in the interior of the catalyst, and thereby improving the catalytic activity, and from the viewpoint of improving the strength of the catalyst, more preferably 85 $\mu$m or less, further preferably 75 $\mu$m or less, furthermore preferably 70 $\mu$m or less, furthermore preferably 68 $\mu$m or less, and furthermore preferably 60 $\mu$m or less.

Moreover, the mode of the pore size of the catalyst is, from the viewpoints of improving the diffusion of raw reaction materials into the interior of the catalyst and the diffusion of reaction products from the interior of the catalyst, and thereby improving the selectivity and the catalytic activity, when an alcohol is produced from an ester obtained from a fatty acid and a monohydric alcohol, further preferably 1 $\mu$m or more, furthermore preferably 10 $\mu$m or more, and furthermore preferably 12 $\mu$m or more and, from the viewpoints of improving the efficiency of contact between the catalyst metal and raw reaction materials in the interior of the catalyst, and thereby improving the catalytic activity, and from the viewpoint of improving the strength of the catalyst, more preferably 40 $\mu$m or less, further preferably 30 $\mu$m or less, furthermore preferably 20 $\mu$m or less, and furthermore preferably 15 $\mu$m or less.

The median of the pore size of the catalyst used in the present invention is, from the viewpoints of improving the diffusion of raw reaction materials into the interior of the catalyst and the diffusion of reaction products from the interior of the catalyst, and thereby improving the catalytic activity, preferably 0.1 $\mu$m or more, more preferably 1 $\mu$m or more, and further preferably 8 $\mu$m or more and, from the viewpoints of improving the efficiency of contact between the catalyst metal and raw reaction materials in the interior of the catalyst, and thereby improving the selectivity and the catalytic activity, preferably 100 $\mu$m or less.

Moreover, the median of the pore size of the catalyst is, from the viewpoints of improving the diffusion of raw reaction materials into the interior of the catalyst and the diffusion of reaction products from the interior of the catalyst, and thereby improving the catalytic activity, when an alcohol is produced from a fatty acid or oil, furthermore preferably 15 μm or more, furthermore preferably 20 μm or more, furthermore preferably 25 μm or more, and furthermore preferably 27 μm or more and, from the viewpoints of improving the efficiency of contact between the catalyst metal and raw reaction materials in the interior of the catalyst, and thereby improving the selectivity and the catalytic activity, more preferably 85 μm or less, further preferably 70 μm or less, furthermore preferably 65 μm or less, furthermore preferably 60 μm or less, furthermore preferably 55 μm or less, furthermore preferably 50 μm or less, and furthermore preferably 49 μm or less.

Moreover, the median of the pore size of the catalyst is, from the viewpoints of improving the diffusion of raw reaction materials into the interior of the catalyst and the diffusion of reaction products from the interior of the catalyst, and thereby improving the catalytic activity, when an alcohol is produced from an ester obtained from a fatty acid and a monohydric alcohol, furthermore preferably 10 μm or more and, from the viewpoints of improving the efficiency of contact between the catalyst metal and raw reaction materials in the interior of the catalyst, and thereby improving the selectivity and the catalytic activity, more preferably 40 μm or less, further preferably 30 μm or less, furthermore preferably 20 μm or less, furthermore preferably 15 μm or less, and furthermore preferably 11 μm or less.

The porosity of the catalyst used in the present invention is, from the viewpoints of improving the diffusion of raw reaction materials into the interior of the catalyst and the diffusion of reaction products from the interior of the catalyst, and thereby improving the selectivity, preferably 30% or more and, from the viewpoints of improving the efficiency of contact between the catalyst metal and raw reaction materials in the interior of the catalyst, and thereby improving the catalytic activity, and from the viewpoint of improving the strength of the catalyst, preferably 99% or less.

Moreover, the porosity of the catalyst is, from the viewpoints of improving the diffusion of raw reaction materials into the interior of the catalyst and the diffusion of reaction products from the interior of the catalyst, and thereby improving the selectivity, when an alcohol is produced from an ester obtained from a fatty acid and a monohydric alcohol, more preferably 35% or more, further preferably 40% or more, furthermore preferably 45% or more, and furthermore preferably 49% or more and, from the viewpoints of improving the efficiency of contact between the catalyst metal and raw reaction materials in the interior of the catalyst, and thereby improving the catalytic activity, and from the viewpoint of improving the strength of the catalyst, more preferably 80% or less, further preferably 75% or less, furthermore preferably 70% or less, and furthermore preferably 67% or less.

Moreover, the porosity of the catalyst is, from the viewpoints of improving the diffusion of raw reaction materials into the interior of the catalyst and the diffusion of reaction products from the interior of the catalyst, and thereby improving the selectivity, when an alcohol is produced from a fatty acid or oil, more preferably 60% or more, further preferably 75% or more, furthermore preferably 80% or more, and furthermore preferably 84% or more and, from the viewpoints of improving the efficiency of contact between the catalyst metal and raw reaction materials in the interior of the catalyst, and thereby improving the catalytic activity, and from the viewpoint of improving the strength of the catalyst, more preferably 90% or less, and further preferably 85% or less.

The specific surface area of the catalyst used in the present invention is, from the viewpoints of improving the diffusion of raw reaction materials into the interior of the catalyst and the diffusion of reaction products from the interior of the catalyst, and thereby improving the selectivity, preferably 0.1 $m^2/g$ or more, more preferably 0.8 $m^2/g$ or more, and more preferably 10 $m^2/g$ or more and, from the viewpoints of improving the efficiency of contact between the catalyst metal and raw reaction materials in the interior of the catalyst, and thereby improving the catalytic activity, and from the viewpoint of improving the strength of the catalyst, preferably 500 $m^2/g$ or less, more preferably 400 $m^2/g$ or less, further preferably 250 $m^2/g$ or less, furthermore preferably 100 $m^2/g$ or less, furthermore preferably 60 $m^2/g$ or less, furthermore preferably 40 $m^2/g$ or less, and furthermore preferably 35 $m^2/g$ or less.

Moreover, the specific surface area of the catalyst is, from the viewpoints of improving the diffusion of raw reaction materials into the interior of the catalyst and the diffusion of reaction products from the interior of the catalyst, and thereby improving the selectivity, when an alcohol is produced from a fatty acid or oil, further preferably 15 $m^2/g$ or more, furthermore preferably 20 $m^2/g$ or more, and furthermore preferably 21 $m^2/g$ or more and, from the viewpoints of improving the efficiency of contact between the catalyst metal and raw reaction materials in the interior of the catalyst, and thereby improving the catalytic activity, and from the viewpoint of improving the strength of the catalyst, furthermore preferably 32 $m^2/g$ or less.

Moreover, the specific surface area of the catalyst is, from the viewpoints of improving the diffusion of raw reaction materials into the interior of the catalyst and the diffusion of reaction products from the interior of the catalyst, and thereby improving the selectivity, when an alcohol is produced from an ester obtained from a fatty acid and a monohydric alcohol, further preferably 14 $m^2/g$ or more and, from the viewpoints of improving the efficiency of contact between the catalyst metal and raw reaction materials in the interior of the catalyst, and thereby improving the catalytic activity, and from the viewpoint of improving the strength of the catalyst, furthermore preferably 30 $m^2/g$ or less, furthermore preferably 20 $m^2/g$ or less, and furthermore preferably 15 $m^2/g$ or less.

The bulk density of the catalyst used in the present invention is, from the viewpoint of improving the strength of the catalyst, and from the viewpoint of increasing the amount of the catalyst filling the reactor, preferably 100 $kg/m^3$ or more, more preferably 200 $kg/m^3$ or more, further preferably 300 $kg/m^3$ or more, and furthermore preferably 400 $kg/m^3$ or more and, from the viewpoints of improving the diffusion of raw reaction materials into the interior of the catalyst and the diffusion of reaction products from the interior of the catalyst with large spaces, and thereby improving the selectivity and the catalytic activity, and from the viewpoint of reducing the pressure loss caused when raw reaction materials or reaction products pass through the interior of the catalyst, preferably 10,000 $kg/m^3$ or less, more preferably 2,500 $kg/m^3$ or less, further preferably 2,000 $kg/m^3$ or less, furthermore preferably 1,500 $kg/m^3$ or less, and furthermore preferably 1,000 $kg/m^3$ or less.

Moreover, the bulk density of the catalyst is, when an alcohol is produced from a fatty acid or an oil, from the viewpoint of improving the strength of the catalyst, and from the viewpoint of increasing the amount of the catalyst filling the reactor, furthermore preferably 500 kg/m³ or more, furthermore preferably 600 kg/m³ or more, and furthermore preferably 680 kg/m³ or more and, from the viewpoints of improving the diffusion of raw reaction materials into the interior of the catalyst and the diffusion of reaction products from the interior of the catalyst with large spaces, and thereby improving the selectivity and the catalytic activity, and from the viewpoint of reducing the pressure loss caused when raw reaction materials or reaction products pass through the interior of the catalyst, furthermore preferably 850 kg/m³ or less, and furthermore preferably 770 kg/m³ or less.

Moreover, the bulk density of the catalyst is, when an alcohol is produced from an ester obtained from a fatty acid and a monohydric alcohol, from the viewpoint of improving the strength of the catalyst, and from the viewpoint of increasing the amount of the catalyst filling the reactor, furthermore preferably 450 kg/m³ or more and, from the viewpoints of improving the diffusion of raw reaction materials into the interior of the catalyst and the diffusion of reaction products from the interior of the catalyst with large spaces, and thereby improving the selectivity and the catalytic activity, and from the viewpoint of reducing the pressure loss caused when raw reaction materials or reaction products pass through the interior of the catalyst, furthermore preferably 600 kg/m³ or less, and furthermore preferably 500 kg/m³ or less.

The total pore volume of the catalyst used in the present invention, the volume of pores with a pore diameter of 0.1 μm or more and 500 μm or less, the mode and the median of the pore size, the porosity, the specific surface area and the bulk density can be measured by the methods described in the Examples.

The shape of the catalyst may be any of a sphere, a cylinder, a sheet, a tube, a honeycomb, an unfixed shape and the like, but a sheet is preferable because it is easy to process the catalyst into a shape according to the use.

When the catalyst is a sheet, the catalyst may be a long band, and for example, a sheet wound into a roll may also be used. When the catalyst is a sheet, the thickness is, from the viewpoint of improving the strength of the catalyst, preferably 0.1 mm or more, more preferably 0.5 mm or more, and further preferably 0.8 mm or more and, from the viewpoints of reducing the diffusion distances of raw reaction materials and reaction products in the interior of the catalyst, thereby improving the diffusion of the raw reaction materials into the interior of the catalyst and the diffusion of the reaction products from the interior of the catalyst, and thereby improving the selectivity and the catalytic activity, preferably 10 mm or less, more preferably 2 mm or less, and further preferably 1.2 mm or less.

The carried amount of the catalyst metal per unit mass of the catalyst used in the present invention is, from the viewpoints of improving the efficiency of contact between the catalyst metal and raw reaction materials in the interior of the catalyst, and thereby improving the catalytic activity, preferably 0.01 g/g or more and, from the viewpoint of improving the selectivity of the catalyst, preferably 0.8 g/g or less.

Moreover, the carried amount of the catalyst metal per unit mass of the catalyst is, when an alcohol is produced from a fatty acid or an oil, from the viewpoints of improving the efficiency of contact between the catalyst metal and raw reaction materials in the interior of the catalyst, and thereby improving the catalytic activity, more preferably 0.3 g/g or more, and further preferably 0.33 g/g or more and, from the viewpoint of improving the selectivity of the catalyst, more preferably 0.6 g/g or less, further preferably 0.5 g/g or less, and furthermore preferably 0.4 g/g or less.

Moreover, the carried amount of the catalyst metal per unit mass of the catalyst is, when an alcohol is produced from an ester obtained from a fatty acid and a monohydric alcohol, from the viewpoints of improving the efficiency of contact between the catalyst metal and raw reaction materials in the interior of the catalyst, and thereby improving the catalytic activity, more preferably 0.1 g/g or more, further preferably 0.15 g/g or more, furthermore preferably 0.2 g/g or more, furthermore preferably 0.25 g/g or more, and furthermore preferably 0.27 g/g or more and, from the viewpoint of improving the selectivity of the catalyst, more preferably 0.35 g/g or less, and further preferably 0.3 g/g or less.

The carried amount of the catalyst metal per unit volume of the catalyst used in the present invention is, as the catalyst metal, from the viewpoints of improving the efficiency of contact between the catalyst metal and raw reaction materials in the interior of the catalyst, and thereby improving the catalytic activity, 0.05 g/mL or more and, from the viewpoint of improving the selectivity of the catalyst, preferably 1.0 g/mL or less.

Moreover, the carried amount of the catalyst metal per unit volume of the catalyst is, as the catalyst metal, when an alcohol is produced from a fatty acid or an oil, from the viewpoints of improving the efficiency of contact between the catalyst metal and raw reaction materials in the interior of the catalyst, and thereby improving the catalytic activity, preferably 0.15 g/mL or more, more preferably 0.2 g/mL or more, further preferably 0.25 g/mL or more, and furthermore preferably 0.3 g/mL or more and, from the viewpoint of improving the selectivity of the catalyst, more preferably 0.8 g/mL or less, further preferably 0.6 g/mL or less, furthermore preferably 0.4 g/mL or less, furthermore preferably 0.35 g/mL or less, and furthermore preferably 0.3 g/mL or less.

Moreover, the carried amount of the catalyst metal per unit volume of the catalyst is, as the catalyst metal, when an alcohol is produced from an ester obtained from a fatty acid and a monohydric alcohol, from the viewpoints of improving the efficiency of contact between the catalyst metal and raw reaction materials in the interior of the catalyst, and thereby improving the catalytic activity, preferably 0.1 g/mL or more, and more preferably 0.12 g/mL or more and, from the viewpoint of improving the selectivity of the catalyst, preferably 0.2 g/mL or less, and more preferably 0.15 g/mL or less.

[Catalyst Metal]

The catalyst used in the present invention contains one or more elements selected from Co and Cu as the catalyst metal. From the viewpoint of producing an alcohol having 8 or more and 22 or less carbon atoms from a fatty acid or an oil, the catalyst preferably contains Co. From the viewpoint of producing an alcohol having 8 or more and 22 or less carbon atoms from an ester obtained from a fatty acid and a monohydric alcohol, the catalyst preferably contains Cu.

Moreover, from the viewpoint of improving the catalytic activity and the selectivity, the catalyst preferably contains a transition metal other than Co and Cu as a promoter component. When two or more kinds of promoter component are used, among the promoter components, the promoter component which is the highest in amount is called the first promoter component; the promoter component which is the second highest in amount is called the second promoter component; and the promoter component which is the third highest in amount is called the third promoter component.

From the viewpoint of improving the catalytic activity and the selectivity, the catalyst preferably contains as the promoter component one or more kinds selected from the group 3 metals, the group 4 metals, the group 5 metals, the group 6 metals, the group 10 metals, the group 12 metals, the group 13 metals and the group 14 metals, and specifically, the catalyst preferably contains one or more elements selected from Zr, Y, La, Ce, Si, Al, Sc, V, Nb, Mo, Pd, Pt, Ti, Cr, Zn, Ba, Fe, Al and Si and more preferably contains one or more elements selected from Zr, Y, Mo, Pd, Ti, Zn and Ba. From the viewpoint of improving the catalytic activity and the selectivity when an alcohol having 8 or more and 22 or less carbon atoms is produced from a fatty acid or an oil, the catalyst further preferably contains one or more elements selected from Zr, Y, Mo and Pd, and from the viewpoint of improving the catalytic activity and the selectivity when an alcohol having 8 or more and 22 or less carbon atoms is produced from an ester obtained from a fatty acid and a monohydric alcohol, the catalyst further preferably contains one or more elements selected from Ti, Zn and Ba. Moreover, from the viewpoint of improving the catalytic activity and the selectivity, the catalyst can contain one or more kinds selected from the elements as the second promoter component and the third promoter component. As the catalyst, for example, Co catalysts such as Co—Mo, Co—Zr, Co—Zr—Mo and Co—Y—Pd—Mo and Cu catalysts such as Cu—Cr, Cu—Zn, Cu—Zn—Ti and Cu—Zn—Ti—Ba can be used. The catalyst metal compound contained in the catalyst used in the present invention is preferably an oxide from the viewpoint of handling.

When one or more kinds of promoter component are used, the total number of moles of the promoter metal(s) based on 100 mol of Co or Cu is, from the viewpoint of improving the catalytic activity and the selectivity, preferably 0.01 or more, and preferably 200 or less. Moreover, the total number of moles of the promoter metal(s) based on 100 mol of Co or Cu is, from the viewpoint of improving the catalytic activity and the selectivity when an alcohol is produced from a fatty acid or an oil, more preferably 0.1 or more, further preferably one or more, and furthermore preferably three or more and, from the viewpoint of improving the selectivity, more preferably 100 or less, further preferably 10 or less, and furthermore preferably six or less. Moreover, the total number of moles of the promoter metal (s) based on 100 mol of Co or Cu is, from the viewpoint of improving the catalytic activity and the selectivity when an alcohol is produced from an ester obtained from a fatty acid and a monohydric alcohol, more preferably 100 or more, and further preferably 110 or more, and more preferably 150 or less, and further preferably 130 or less.

The number of moles of the first promoter metal based on 100 mol of Co or Cu is, from the viewpoint of improving the catalytic activity and the selectivity, preferably 0.001 or more, and preferably 200 or less. Moreover, the number of moles of the first promoter metal based on 100 mol of Co or Cu is, from the viewpoint of improving the catalytic activity and the selectivity when an alcohol is produced from a fatty acid or oil, more preferably 0.01 or more, further preferably 0.1 or more, furthermore preferably one or more, and furthermore preferably 1.5 or more and, from the viewpoint of improving the selectivity, more preferably 100 or less, further preferably 10 or less, and furthermore preferably four or less. Moreover, the number of moles of the first promoter metal based on 100 mol of Co or Cu is, from the viewpoint of improving the catalytic activity and the selectivity when an alcohol is produced from an ester obtained from a fatty acid and a monohydric alcohol, more preferably 100 or more, and further preferably 110 or more, and more preferably 150 or less, and further preferably 120 or less.

The number of moles of the second promoter metal based on 100 mol of Co or Cu is, from the viewpoint of improving the catalytic activity and the selectivity, preferably 0.0001 or more, and preferably 10 or less. Moreover, the number of moles of the second promoter metal based on 100 mol of Co or Cu is, from the viewpoint of improving the catalytic activity and the selectivity when an alcohol is produced from a fatty acid or an oil, more preferably 0.001 or more, further preferably 0.01 or more, furthermore preferably 0.1 or more, and furthermore preferably one or more, and more preferably four or less, and further preferably two or less. Moreover, the number of moles of the second promoter metal based on 100 mol of Co or Cu is, from the viewpoint of improving the catalytic activity and the selectivity when an alcohol is produced from an ester obtained from a fatty acid and a monohydric alcohol, more preferably 0.1 or more, further preferably one or more, and furthermore preferably four or more, and more preferably eight or less, and further preferably six or less.

The number of moles of the third promoter metal based on 100 mol of Co or Cu is, from the viewpoint of improving the catalytic activity and the selectivity, preferably 0.0001 or more, and preferably 10 or less. Moreover, the number of moles of the third promoter metal based on 100 mol of Co or Cu is, from the viewpoint of improving the catalytic activity when an alcohol is produced from a fatty acid or an oil, more preferably 0.001 or more, further preferably 0.01 or more, and furthermore preferably 0.05 or more and, from the viewpoint of improving the catalytic activity and the selectivity when an alcohol is produced from a fatty acid or an oil, more preferably one or less, further preferably 0.2 or less, and furthermore preferably 0.1 or less. Moreover, the number of moles of the third promoter metal based on 100 mol of Co or Cu is, from the viewpoint of improving the catalytic activity and the selectivity when an alcohol is produced from an ester obtained from a fatty acid and a monohydric alcohol, more preferably 0.1 or more, further preferably one or more, furthermore preferably three or more, and furthermore preferably four or more and, from the same viewpoint, more preferably eight or less, further preferably six or less, and furthermore preferably five or less.

[Support of Catalyst]

A porous structure is preferably used as the support of the catalyst used in the present invention, from the viewpoints of improving the diffusion of raw reaction materials into the interior of the catalyst and the diffusion of reaction products from the interior of the catalyst, and thereby improving the selectivity and the catalytic activity, and from the viewpoints of improving the efficiency of contact between the catalyst metal and a fatty acid or a fatty acid ester in the interior of the catalyst, and thereby improving the catalytic activity. From the viewpoint of heat resistance, the constituent material of the porous structure is preferably a metal such as Al, Ni, Cu, Ti, Fe and Co, an alloy such as Al alloy, Ti alloy and stainless or ceramics such as silica, alumina, silica-alumina, calcia-magnesia-silica, titania, zirconia, silicon carbide, mullite, cordierite, silicon nitride, aluminum nitride, barium titanate, zinc oxide, calcium oxide and magnesium oxide, and more preferably ceramics.

From the viewpoints of improving the diffusion of raw reaction materials into the interior of the catalyst and the diffusion of reaction products from the interior of the catalyst, and thereby improving the selectivity and the catalytic activity, and from the viewpoints of improving the efficiency of contact between the catalyst metal and a fatty acid or a fatty acid ester in the interior of the catalyst, and thereby improving the catalytic activity, the ceramics are more preferably silica, alumina, silica-alumina, calcia-magnesia-silica, titania or zirconia, further preferably silica, alumina, silica-alumina or calcia-magnesia-silica, and furthermore preferably silica-alumina or calcia-magnesia-silica.

The total pore volume of the porous structure is, from the viewpoints of improving the diffusion of raw reaction materials into the interior of the catalyst and the diffusion of reaction products from the interior of the catalyst, and thereby improving the selectivity and the catalytic activity, preferably 0.1 mL/g or more, more preferably 0.15 mL/g or more, further preferably 0.6 mL/g or more, furthermore preferably 0.9 mL/g or more, furthermore preferably 1 mL/g or more, furthermore preferably 1.1 mL/g or more, furthermore preferably 1.2 mL/g or more, furthermore preferably 2 mL/g or more, furthermore preferably 3 mL/g or more, and furthermore preferably 3.5 mL/g or more and, from the viewpoints of improving the efficiency of contact between the catalyst metal and raw reaction materials in the interior of the catalyst, and thereby improving the catalytic activity, and from the viewpoint of improving the strength of the catalyst, preferably 10 mL/g or less, more preferably 7.5 mL/g or less, further preferably 7 mL/g or less, and furthermore preferably 5 mL/g or less.

The volume of pores with a pore size of 0.1 µm or more and 500 µm or less in the porous structure is, from the viewpoints of improving the diffusion of raw reaction materials into the interior of the catalyst and the diffusion of reaction products from the interior of the catalyst, and thereby improving the selectivity and the catalytic activity, based on the total pore volume, preferably 50% or more, more preferably 80% or more, further preferably 90% or more, and furthermore preferably 95% or more and, from the viewpoints of improving the efficiency of contact between the catalyst metal and raw reaction materials in the interior of the catalyst, and thereby improving the catalytic activity, preferably 100% or less.

The mode of the pore size of the porous structure is, from the viewpoints of improving the diffusion of raw reaction materials into the interior of the catalyst and the diffusion of reaction products from the interior of the catalyst, and thereby improving the selectivity and the catalytic activity, preferably 0.1 µm or more, more preferably 1 µm or more, further preferably 10 µm or more, and furthermore preferably 20 µm or more and, from the viewpoints of improving the efficiency of contact between the catalyst metal and raw reaction materials in the interior of the catalyst, and thereby improving the catalytic activity, and from the viewpoint of improving the strength of the catalyst, preferably 500 µm or less, more preferably 200 µm or less, further preferably 100 µm or less, and furthermore preferably 60 µm or less.

The median of the pore size of the porous structure is, from the viewpoints of improving the diffusion of raw reaction materials into the interior of the catalyst and the diffusion of reaction products from the interior of the catalyst, and thereby improving the selectivity and the catalytic activity, preferably 0.1 µm or more, more preferably 1 µm or more, further preferably 10 µm or more, and furthermore preferably 20 µm or more and, from the viewpoints of improving the efficiency of contact between the catalyst metal and raw reaction materials in the interior of the catalyst, and thereby improving the catalytic activity, and from the viewpoint of improving the strength of the catalyst, preferably 500 µm or less, more preferably 200 µm or less, further preferably 140 µm or less, furthermore preferably 100 µm or less, and furthermore preferably 60 µm or less.

The porosity of the porous structure is, from the viewpoints of improving the diffusion of raw reaction materials into the interior of the catalyst and the diffusion of reaction products from the interior of the catalyst, and thereby improving the selectivity and the catalytic activity, preferably 30% or more, more preferably 40% or more, further preferably 50% or more, furthermore preferably 55% or more, furthermore preferably 60% or more, and furthermore preferably 70% or more and, from the viewpoints of improving the efficiency of contact between the catalyst metal and raw reaction materials in the interior of the catalyst, and thereby improving the catalytic activity, and from the viewpoint of improving the strength of the catalyst, preferably 99% or less, more preferably 95% or less, and further preferably 93% or less.

The bulk density of the porous structure is, from the viewpoint of improving the strength of the catalyst, and from the viewpoint of increasing the amount of the catalyst filling the reactor, preferably 10 $kg/m^3$ or more, more preferably 100 $kg/m^3$ or more, and further preferably 150 $kg/m^3$ or more and, from the viewpoints of improving the diffusion of raw reaction materials into the interior of the catalyst and the diffusion of reaction products from the interior of the catalyst with large spaces, and thereby improving the selectivity and the catalytic activity, and from the viewpoint of reducing the pressure loss caused when raw reaction materials or reaction products pass through the interior of the catalyst, preferably 7,000 $kg/m^3$ or less, more preferably 4,000 $kg/m^3$ or less, further preferably 2,400 $kg/m^3$ or less, furthermore preferably 1,000 $kg/m^3$ or less, furthermore preferably 500 $kg/m^3$ or less, furthermore preferably 300 $kg/m^3$ or less, and furthermore preferably 250 $kg/m^3$ or less.

The total pore volume of the porous structure, the volume of pores with a pore diameter of 0.1 µm or more and 500 µm or less, the mode and the median of the pore size, the porosity, the specific surface area and the bulk density can be measured by the methods described in the Examples.

The porous structure is preferably a fiber structure or a porous compact from the viewpoint of increasing the carried amount of the catalyst metal, and from the viewpoint of improving the strength of the catalyst, and the porous structure is more preferably a fiber structure from the viewpoint of increasing the carried amount of the catalyst metal, and from the viewpoints of improving the diffusion of raw reaction materials into the interior of the catalyst and the diffusion of reaction products from the interior of the catalyst, and thereby improving the selectivity and the catalytic activity.

The fiber structure used in the present invention is aggregated fibers. From the viewpoints of easiness in carrying the catalyst and in processing the catalyst, the fiber structure is preferably woven fabric, knitted fabric or a nonwoven cloth, and more preferably a nonwoven cloth. When the fiber structure is used, the shape of the fiber structure is, from the viewpoint of workability, preferably a sheet, a tube, a honeycomb or an unfixed shape, and from the viewpoint of easiness in processing the obtained catalyst into a shape according to the use, more preferably a sheet. In addition, from the viewpoint of improving the productivity of the fiber structure, the fiber structure is preferably produced by a wet papermaking method or a dry papermaking method.

When a fiber structure sheet is used as the support, the thickness of the fiber structure is, from the viewpoint of improving the strength of the catalyst, preferably 0.1 mm or more, more preferably 0.5 mm or more, and further preferably 0.8 mm or more and, from the viewpoints of reducing the diffusion distances of raw reaction materials and reaction products in the interior of the catalyst, thereby improving the diffusion of the raw reaction materials into the interior of the catalyst and the diffusion of the reaction products from the interior of the catalyst, and thereby improving the selectivity and the catalytic activity, preferably 10 mm or less, more preferably 5 mm or less, further preferably 2 mm or less, and furthermore preferably 1.2 mm or less.

The aspect ratio of the fibers of the fiber structure (the ratio of the fiber length to the diameter of the cross section of the fibers) is, from the viewpoint of increasing the carried amount of the catalyst metal, preferably five or more, more preferably 10 or more, and further preferably 20 or more and, from the viewpoints of maintaining the shape of the fiber structure and maintaining the catalytic activity, preferably 100,000 or less, more preferably 10,000 or less, further preferably 5,000 or less, and furthermore preferably 1,000 or less.

The mean diameter of the fibers is, from the viewpoints of maintaining the shape of the fiber structure and maintaining the catalytic activity, preferably 100 nm or more, more preferably 200 nm or more, further preferably 500 nm or more, and furthermore preferably 1,000 nm or more and, from the viewpoint of increasing the carried amount of the catalyst metal, preferably 50,000 nm or less, more preferably 30,000 nm or less, and further preferably 10,000 nm or less.

The mean length of the fibers is, from the viewpoint of increasing the carried amount of the catalyst metal, preferably 0.5 µm or more, more preferably 5 µm or more, further preferably 20 µm or more, and furthermore preferably 60 µm or more and, from the viewpoint of availability, preferably 500,000 µm or less, more preferably 50,000 µm or less, further preferably 30,000 µm or less, and furthermore preferably 10,000 µm or less.

From the viewpoint of heat resistance, the fibers are preferably made of a combination of one or two or more kinds of fiber selected from ceramic fibers and metal fibers, and more preferably ceramic fibers. From the viewpoints of heat resistance and availability, the ceramic fibers are preferably silica fibers, alumina fibers, silica-alumina fibers, calcia-magnesia-silica fibers, titania fibers or zirconia fibers, and more preferably silica-alumina fibers or calcia-magnesia-silica fibers. From the viewpoint of improving the productivity, the fibers are preferably produced by a spinning method or a blowing method.

The porous compact used in the present invention is a compact obtained by molding particles of a metal, an alloy or ceramics and then fusion bonding the particles by heating or the like. The particles constituting the compact are fusion bonded to each other in the compact to form a strong network, and due to this network, the compact carries the catalyst metal and has enough space for the diffusion of raw reaction materials and reaction products. In addition, its external size is suitable for the catalyst used in fixed bed reaction process.

When a porous compact is used as the porous structure in the present invention, the porous compact may have an unfixed shape or a shape such as a sphere or a cylinder, but from the viewpoint of the amount of the catalyst which fills the reactor, the shape is preferably a sphere or a cylinder, and more preferably a sphere.

When a spherical porous compact is used as the porous structure, the outer diameter is, from the viewpoint of using for a catalyst used in fixed bed reaction process, and from the viewpoint of reducing the pressure loss caused when raw reaction materials or reaction products pass through the catalyst-filled layer, preferably 0.1 mm or more, more preferably 0.5 mm or more, further preferably 1 mm or more, and furthermore preferably 4 mm or more and, from the viewpoint of increasing the amount of the catalyst filling the reactor, preferably 100 mm or less, more preferably 50 mm or less, further preferably 10 mm or less, and furthermore preferably 6 mm or less.

From the viewpoints of heat resistance and availability, the porous compact is preferably ceramics such as silica, alumina, alumina-silica, titania or zirconia.

[Production Method of Catalyst]

From the viewpoint of increasing the carried amount of the catalyst metal, the method for producing the catalyst used in the present invention is preferably a method in which a catalyst precursor or a catalyst metal oxide is carried on a support and then calcined. Here, the catalyst precursor is a compound which is converted to a catalyst metal oxide by calcining.

The method for carrying a catalyst precursor or a catalyst metal oxide on a support is an impregnation method, a co-precipitation method or a homogeneous mixing method. Among them, from the viewpoint of increasing the carried amount of the catalyst metal, and from the viewpoints of improving the efficiency of contact between the catalyst metal and raw reaction materials in the interior of the catalyst, and thereby improving the catalytic activity, the method is preferably an impregnation method, namely an impregnation method by immersing a support in a slurry containing a catalyst precursor or a catalyst metal oxide. In this regard, a slurry containing a catalyst precursor and a slurry containing a catalyst metal oxide are also called a catalyst precursor coating material and a catalyst metal oxide coating material, respectively. In this case, the step of preparing a coating material of a catalyst precursor or a catalyst metal oxide, the carrying step and the calcining step are conducted in this order in the production step of the catalyst.

(Coating Material Preparation Step)

The coating material preparation step is a step in which a catalyst precursor coating material or a catalyst metal oxide coating material is produced by dispersing a catalyst precursor or a catalyst metal oxide in a dispersion medium.

From the viewpoint of improving the catalytic activity, and from the viewpoint of availability of raw materials, the catalyst precursor is preferably a solution of a compound containing the same element as the catalyst metal, more preferably a solution of a salt of the same element as the catalyst metal and a strong acid or of an amine complex of the same element as the catalyst metal, and further preferably a catalyst precursor precipitated by adding an alkali agent to a solution of a salt of the same element as the catalyst metal and a strong acid. Here, the strong acid means an inorganic acid with an acid dissociation constant pKa in an aqueous solution at 25° C. of less than 0 or sulfuric acid. From the viewpoint of improving the catalytic activity, and from the viewpoint of availability of raw materials, the salt of the same element as the catalyst metal and the strong acid is preferably nitrate, sulfate or hydrochloride, from the viewpoint of improving the catalytic activity, further preferably nitrate or sulfate and furthermore preferably nitrate. From the viewpoint of improving the catalytic activity, the precipitated catalyst precursor is preferably dispersed in a dispersion medium to prepare a slurry, after filtration through a filter, separation from the liquid phase by a method such as centrifugation, washing with water such as deionized water, drying or the like.

The alkali agent used for precipitating the catalyst precursor is, from the viewpoint of improving the catalytic activity, and from the viewpoint of availability of raw materials, preferably hydroxide or carbonate of an alkali metal, more preferably carbonate of an alkali metal, and from the viewpoint of improving the catalytic activity, furthermore preferably sodium carbonate or ammonium carbonate. From the viewpoint of workability in precipitating the catalyst precursor, the alkali agent is preferably used as a solution.

From the viewpoint of improving the catalytic activity, and from the viewpoint of availability of raw materials, the solvent used for precipitating the catalyst precursor is preferably one or more kinds selected from water and hydrophilic solvents, more preferably one or more kinds selected from water and alcohols having one or more and three or less carbon atoms, further preferably one or more kinds selected from water, methanol, ethanol and isopropanol, further preferably one or more kinds selected from water and isopropanol, and furthermore preferably water. The embodiments of the solvents used for the solution of the salt of the raw material of the catalyst precursor and the strong acid and the solution of the alkali agent are the same as the embodiments of the solvent used for precipitating the catalyst precursor.

Moreover, a catalyst metal oxide can be produced by calcining the obtained catalyst precursor before the catalyst precursor is carried on a support. This step is called a preliminary calcining step. The temperature of the preliminary calcining is, from the viewpoint of improving the catalytic activity and the selectivity, preferably 300° C. or higher, and more preferably 500° C. or higher, and preferably 800° C. or lower, and more preferably 700° C. or lower. The period of the preliminary calcining is, from the viewpoint of improving the catalytic activity and the selectivity, preferably two hours or longer, and more preferably three hours or longer and, from the viewpoint of improving the productivity, preferably 10 hours or shorter, and more preferably five hours or shorter.

From the viewpoint of carrying the catalyst precursor or the catalyst metal oxide simply on the porous structure, the dispersion medium of the catalyst precursor coating material or the catalyst metal oxide coating material is preferably one or more kinds selected from water and hydrophilic solvents, more preferably one or more kinds selected from water and alcohols having one or more and three or less carbon atoms, further preferably one or more kinds selected from water, methanol, ethanol and isopropanol, and further preferably one or more kinds selected from water and isopropanol. The catalyst precursor coating material or the catalyst metal oxide coating material may contain a dispersing agent. The dispersing agent is a polymeric dispersing agent, a surfactant-type dispersing agent or an inorganic dispersing agent, and from the viewpoint of improving the dispersibility of the particles of the catalyst precursor or the catalyst metal oxide in the catalyst precursor coating material or the catalyst metal coating material, a polymeric dispersing agent is preferable.

From the viewpoints of binding the catalyst metal oxide and the porous structure in the calcining step and increasing the carried amount of the catalyst metal, the coating material preferably contains a binder. From the viewpoint of increasing the carried amount of the catalyst metal, and from the viewpoint of maintaining the catalytic activity, the binder is preferably an oxide of a metal other than the catalyst metal, more preferably one or more kinds selected from the group consisting of aluminum oxide, silicon oxide, antimony oxide, titanium oxide, zirconium oxide, magnesium oxide and calcium oxide, more preferably one or more kinds selected from aluminum oxide, titanium oxide, zirconium oxide, magnesium oxide and silicon oxide, and further preferably zirconium oxide.

From the viewpoint of increasing the carried amount of the catalyst metal, the binder is added to the catalyst precursor coating material or the catalyst metal oxide coating material, preferably as a powder of the binder, a sol of the binder or a slurry prepared by dispersing the binder in a solvent, and more preferably as a powder of the binder or a sol of the binder.

The concentration of the catalyst precursor or the catalyst metal oxide in the catalyst precursor coating material or the catalyst metal coating material is, from the viewpoint of increasing the carried amount of the catalyst metal, preferably 1% by mass or more, more preferably 5% by mass or more, further preferably 15% by mass or more, and furthermore preferably 20% by mass or more and, from the viewpoint of improving the dispersibility of the catalyst precursor or the catalyst metal oxide in the catalyst precursor coating material or the catalyst metal oxide coating material, preferably 40% by mass or less, and more preferably 35% by mass or less.

The binder content in the coating material is, from the viewpoint of increasing the carried amount of the catalyst metal, and from the viewpoint of maintaining the catalytic activity, based on the catalyst precursor or the catalyst metal oxide, preferably 1% by mass or more, and more preferably 5% by mass or more and, from the viewpoint of increasing the carried amount of the catalyst metal, preferably 30% by mass or less, more preferably 25% by mass or less, further preferably 20% by mass or less, and furthermore preferably 10% by mass or less.

The mean particle size of the catalyst precursor or the catalyst metal oxide in the catalyst precursor coating material or the catalyst metal oxide coating material is, from the viewpoint of increasing the carried amount of the catalyst metal, and from the viewpoint of improving the dispersibility of the catalyst precursor or the catalyst metal oxide in the coating material, preferably 100 μm or less, more preferably 10 μm or less, further preferably 7 μm or less, furthermore preferably 2 μm or less, and furthermore preferably 1.8 μm or less and, from the viewpoints of improving the productivity of the catalyst precursor coating material or the catalyst metal oxide coating material and the dispersibility of the catalyst precursor or the catalyst metal oxide, preferably 0.1 μm or more, more preferably 0.2 μm or more, further preferably 0.3 μm or more, further preferably 0.6 μm or more, and furthermore preferably 1 μm or more. The mean particle size of the catalyst precursor or the catalyst metal oxide can be adjusted to the above value by wet dispersion or the like. The mean particle size of the catalyst precursor or the catalyst metal oxide in the catalyst precursor coating material or the catalyst metal oxide coating material can be measured by the method described in the Examples.

In the coating material preparation step, the necessary components can be mixed in one stage using a media mill or a paint shaker to prepare a coating material, but it is preferable to prepare a coating material in two mixing stages of preliminary mixing and subsequent main mixing. It is preferable to produce a catalyst precursor coating material or a catalyst metal oxide coating material with a small particle size in two mixing stages of preliminary mixing and main mixing as described above, because the catalyst precursor coating material or the catalyst metal oxide coating material easily enters the spaces in the support in the carrying step which is conducted next. In addition, a mixing method using a non-media disperser can also be applied.

(Carrying Step)

The carrying step is a step in which the catalyst precursor coating material or the catalyst metal oxide coating material obtained in the coating material preparation step is carried on a support. As the method for carrying the catalyst precursor coating material or the catalyst metal oxide coating material on a support, from the viewpoints of uniformly carrying the catalyst precursor or catalyst metal oxide coating material and increasing the amount carried per volume, a method in which the catalyst precursor coating material or the catalyst metal oxide coating material is brought into contact with the support or a method in which an external force is applied to the catalyst precursor coating material or the catalyst metal oxide coating material which is in contact with the support can be preferably applied. As the method for bringing the catalyst precursor coating material or the catalyst metal oxide coating material into contact with the support, a method in which the support is immersed in the catalyst precursor coating material or the catalyst metal oxide coating material can be applied. As the method for applying an external force, a method using a roller or a method of applying ultrasonic vibrations can be applied.

After the carrying step, a step of removing excess catalyst precursor coating material or catalyst metal oxide coating material can be conducted if necessary. By conducting this step, the removal rate of the catalyst precursor or the catalyst metal oxide in the shaping step described below can be decreased.

The support from which the excess catalyst precursor coating material or catalyst metal oxide coating material has been removed is dried if necessary. The drying may be heat drying or natural drying, but from the viewpoint of improving the productivity, heat drying is preferable, and a method of heat drying at a temperature same as or higher than the boiling point of the solvent used in the coating material preparation step is preferable. In this case, the support can be compressed at the same time to control the pores of the catalyst. That is, in the drying step, spaces, namely pores, generate in the support when the solvent is evaporated and removed by drying, resulting in a high porosity, and the pore size and the pore volume can be adjusted by controlling the pores by compression.

The specific temperature of the drying is, from the viewpoints of sufficiently removing the solvent and improving the catalytic activity, preferably 30° C. or higher, more preferably 80° C. or higher, and further preferably 100° C. or higher and, from the viewpoints of reducing the facility load and energy consumption, preferably 150° C. or lower, and more preferably 140° C. or lower. In addition, the period of the drying is, from the viewpoints of sufficiently removing the solvent and improving the catalytic activity, preferably 0.1 hours or longer, and more preferably 0.5 hours or longer and, from the viewpoint of improving the catalytic activity, and from the viewpoint of improving the productivity, preferably 24 hours or shorter, more preferably five hours or shorter, and further preferably two hours or shorter.

(Calcining Step)

The calcining step is a step in which the catalyst precursor or the catalyst metal oxide carried on the support in the carrying step is calcined. In this step, the catalyst metal oxide binds to the support through the binder or directly. Moreover, when a catalyst precursor coating material is used in the carrying step, the catalyst precursor is converted to a catalyst metal oxide, and the generated catalyst metal oxide binds to the support through the binder or directly.

The temperature of the calcining is, from the viewpoints of binding the catalyst metal oxide to the support and improving the catalytic activity and the selectivity, preferably 300° C. or higher, and more preferably 500° C. or higher, and preferably 800° C. or lower, and more preferably 700° C. or lower. Moreover, the period of the calcining is, from the viewpoints of binding the catalyst metal oxide to the support and improving the catalytic activity and the selectivity, preferably two hours or longer, and more preferably three hours or longer and, from the viewpoint of improving the productivity, preferably 24 hours or shorter, more preferably 10 hours or shorter, and further preferably five hours or shorter. The calcining step is preferably conducted in air atmosphere at atmospheric pressure.

After drying in the carrying step or after the calcining step, a shaping step for processing the shape may be conducted depending on the kind of support such as a fiber structure. Through the shaping step, the shape of the catalyst can be changed according to the use. Shaping includes cutting, deformation and the like, and the shape can be changed into a honeycomb, a cylinder, a multilayer roll of a sheet or the like.

The carried amount of the catalyst metal oxide and the binder per unit volume of the catalyst is, from the viewpoints of improving the efficiency of contact between the catalyst metal and raw reaction materials in the interior of the catalyst, and thereby improving the catalytic activity, preferably 0.05 g/mL or more, more preferably 0.1 g/mL or more, further preferably 0.2 g/mL or more, furthermore preferably 0.25 g/mL or more, furthermore preferably 0.3 g/mL or more, furthermore preferably 0.4 g/mL or more, and furthermore preferably 0.5 g/mL or more and, from the viewpoint of improving the selectivity of the catalyst, and from the viewpoint of reducing the pressure loss caused when raw reaction materials or reaction products pass through the interior of the catalyst, preferably 2 g/mL or less. The carried amount of the catalyst metal oxide and the binder per unit volume of the catalyst can be calculated by the method described in the Examples.

Moreover, when an alcohol is produced from a fatty acid or an oil, the carried amount of the catalyst metal oxide and the binder per unit volume of the catalyst is, from the viewpoints of improving the efficiency of contact between the catalyst metal and raw reaction materials in the interior of the catalyst, and thereby improving the catalytic activity, furthermore preferably 0.52 g/mL or more and, from the viewpoint of improving the selectivity of the catalyst, and from the viewpoint of reducing the pressure loss caused when raw reaction materials or reaction products pass through the interior of the catalyst, more preferably 1 g/mL or less, further preferably 0.8 g/mL or less, and furthermore preferably 0.7 g/mL or less.

Moreover, when an alcohol is produced from an ester obtained from a fatty acid and a monohydric alcohol, the carried amount of the catalyst metal oxide and the binder per unit volume of the catalyst is, from the viewpoints of improving the efficiency of contact between the catalyst metal and raw reaction materials in the interior of the catalyst, and thereby improving the catalytic activity, furthermore preferably 0.8 g/mL or more, and furthermore preferably 1 g/mL or more and, from the viewpoint of improving the selectivity of the catalyst, and from the viewpoint of reducing the pressure loss caused when raw reaction materials or reaction products pass through the interior of the catalyst, more preferably 1.5 g/mL or less, and further preferably 1.2 g/mL or less.

<Production of Alcohol>
[Reduction of Catalyst]

According to the method for producing an alcohol of the present invention, the catalyst is preferably reduced before the hydrogenation. The catalyst is activated by the reduction. From the viewpoint of improving the productivity, the reducing agent is preferably hydrogen, carbon monoxide, formaldehyde or the like, and more preferably hydrogen. When a reducing agent of a gas type is used, the reducing agent may be used alone, or the reducing agent may be mixed with an inert gas such as nitrogen or water vapor.

When hydrogen is used for the reduction, a gas phase system in which hydrogen gas is brought into contact with a dry catalyst may be used, and a liquid phase system in which the catalyst is immersed in a liquid and hydrogen is flown may be also used. As the liquid, hydrocarbon such as liquid paraffin, an aliphatic alcohol, an aliphatic ester, carboxylic acid or the like can be used. When a catalyst metal of Co type is used, from the viewpoint of improving the catalytic activity, the reduction is more preferably conducted in a gas phase system. When a catalyst metal of Cu type is used, from the viewpoint of improving the catalytic activity, the reduction is more preferably conducted in a liquid phase system.

When hydrogen is used as the reducing agent and when the catalyst is reduced and activated in a gas phase system, from the viewpoint of improving the catalytic activity, the reduction is conducted in hydrogen flow preferably at 300° C. or higher, more preferably at 400° C. or higher, and further preferably at 450° C. or higher, and the reduction is conducted preferably at 800° C. or lower, more preferably at 600° C. or lower, and further preferably at 550° C. or lower. Hydrogen used here may be 100% hydrogen or may be diluted with an inert gas. Diluted hydrogen is preferable to prevent heat generation due to rapid reduction, and the concentration of diluted hydrogen is, from the viewpoint of improving the productivity, preferably 0.1% by volume or more, more preferably 1% by volume or more, and further preferably 3% by volume or more and, from the viewpoint of facility load, preferably 10% by volume or less, and more preferably 5% by volume or less. The reduction is desirably conducted until the absorption of hydrogen stops. Specifically, from the viewpoint of improving the catalytic activity, the period of the reduction is preferably 0.1 hours or longer, more preferably one hour or longer, and further preferably four hours or longer and, from the viewpoint of improving the productivity, preferably 24 hours or shorter, more preferably 12 hours or shorter, and further preferably six hours or shorter.

The catalyst metal which has been reduced and activated may react strongly with oxygen in the air and generate heat when the catalyst metal is left in the air as it is. Thus, it is preferable to form an oxide film over the surface of the catalyst metal which has been reduced and activated to stabilize the catalyst metal. From the viewpoint of stabilizing the catalyst metal which has been reduced and activated, the oxidation stabilization is conducted in a flow of an inert gas, such as nitrogen, containing oxygen in an amount of preferably 0.1% by volume or more, and more preferably 0.5% by volume or more, and preferably 5% by volume or less, and more preferably 1.5% by volume or less. From the same viewpoint, the temperature of the oxidation stabilization is preferably 0° C. or higher, and more preferably 20° C. or higher, and preferably 200° C. or lower, more preferably 100° C. or lower, and further preferably 50° C. or lower. The period of the oxidation stabilization is, from the same viewpoint, preferably one hour or longer, more preferably five hours or longer, and further preferably seven hours or longer and, from the viewpoint of improving the productivity, preferably 24 hours or shorter, more preferably 12 hours or shorter, and further preferably nine hours or shorter.

When hydrogen is used as the reducing agent and when the catalyst is reduced and activated in a liquid phase system, from the viewpoint of improving the catalytic activity, the reduction is conducted in hydrogen flow preferably at 100° C. or higher, and more preferably at 150° C. or higher, and the reduction is conducted preferably at 300° C. or lower, and more preferably at 200° C. or lower. The hydrogen concentration of hydrogen used is preferably 100% by volume from the viewpoint of improving the catalytic activity. Hydrogen diluted with the inert gas can be used to prevent heat generation due to rapid reduction. The hydrogen concentration in this case is, from the viewpoint of improving the catalytic activity, preferably 0.1% by volume or more, more preferably 1% by volume or more, further preferably 10% by volume or more, furthermore preferably 30% by volume or more, furthermore preferably 50% by volume or more, furthermore preferably 70% by volume or more, and furthermore preferably 90% by volume or more. The reduction is desirably conducted until the absorption of hydrogen stops. Specifically, from the viewpoint of improving the catalytic activity, the period of the reduction is preferably 0.1 hours or longer, and more preferably one hour or longer and, from the viewpoint of improving the productivity, preferably 48 hours or shorter, and more preferably 24 hours or shorter. It is preferable to subject the catalyst which has been reduced and activated directly to the reaction from the viewpoint of production efficiency.

[Hydrogenation]

The method for producing an alcohol of the present invention is a method for producing an aliphatic alcohol having 8 or more and 22 or less carbon atoms through hydrogenation of the fatty acid or the fatty acid ester as the raw material using the catalyst having the specific pore structure. The method for producing an alcohol of the present invention is a continuous, batch or semi-batch process, and preferably a continuous process from the viewpoint of improving the productivity. The apparatus for conducting the hydrogenation is a tubular apparatus filled with the catalyst or a tank apparatus filled with the catalyst, and preferably a tubular apparatus filled with the catalyst from the viewpoint of improving the productivity. From the viewpoint of improving the productivity, the hydrogenation is preferably conducted by a continuous process by passing liquid of the fatty acid or the fatty acid ester through a tubular apparatus filled with the catalyst. The continuous reaction process by passing liquid of the fatty acid or the fatty acid ester through a tubular apparatus filled with the catalyst is also called fixed bed reaction process.

From the viewpoint of reactivity, the reaction temperature is preferably 150° C. or higher, more preferably 180° C. or higher, and further preferably 200° C. or higher, and preferably 300° C. or lower, more preferably 280° C. or lower, and further preferably 250° C. or lower. From the viewpoint of reactivity, the reaction pressure as gauge pressure is preferably 1 MPa or higher, more preferably 5 MPa or higher, further preferably 10 MPa or higher, furthermore preferably 15 MPa or higher, and furthermore preferably 20 MPa or higher and, from the viewpoint of facility load, preferably 30 MPa or lower, and more preferably 27 MPa or lower.

When the hydrogenation is conducted by fixed bed reaction process, the liquid hourly space velocity (LHSV) is determined according to the reaction condition, but from the viewpoints of productivity and reactivity, the LHSV is preferably 0.01 [1/hr] or more, more preferably 0.1 [1/hr] or more, and further preferably 0.2 [1/hr] or more, and preferably 10 [1/hr] or less, and more preferably 1 [1/hr] or less. Moreover, when the hydrogenation is conducted by fixed bed reaction process, from the viewpoint of reactivity, the hydrogen flow rate based on the mole of the raw material fatty acid or fatty acid ester is preferably 0.1 mol/mol or more, more preferably 0.5 mol/mol or more, and further preferably 1 mol/mol or more, and preferably 300 mol/mol or less, more preferably 150 mol/mol or less, and further preferably 100 mol/mol or less.

The amount of the catalyst used can be determined depending on the reaction temperature or the reaction pressure in the range in which a practical reaction rate is achieved, but when the reaction is conducted by batch process, from the viewpoint of reactivity, the amount of the catalyst is, as the mass of Cu or Co metal based on the fatty acid or the fatty acid ester, preferably 0.1% by mass or more, and more preferably 0.5% by mass or more, and preferably 20% by mass or less, more preferably 10% by mass or less, further preferably 5% by mass or less, and furthermore preferably 1.5% by mass or less.

A solvent can be used for the reaction, but it is desirable to conduct the reaction without any solvent considering the productivity. As the solvent, a solvent which does not adversely affect the reaction, such as alcohols, ethers including dioxane and hydrocarbons, is selected.

The present invention further discloses the following production methods regarding the above embodiments.
<1>
A method for producing an aliphatic alcohol having 8 or more and 22 or less carbon atoms through hydrogenation of a fatty acid or a fatty acid ester using a catalyst in which the catalyst carries a catalyst metal on a support, (a) the catalyst contains one or more elements selected from Co and Cu as the catalyst metal, (b) the total pore volume of the catalyst is 0.05 mL/g or more, and (c) the volume of pores with a pore size of 0.1 μm or more and 500 μm or less is 50% or more of the total pore volume of the catalyst.

<2>
The method for producing an aliphatic alcohol described in <1> in which the total pore volume of the catalyst is preferably 0.15 mL/g or more, further preferably 0.5 mL/g or more, and furthermore preferably 0.6 mL/g or more, and preferably 10 mL/g or less, more preferably 4 mL/g or less, further preferably 2.5 mL/g or less, furthermore preferably 1.6 mL/g or less, and furthermore preferably 1 mL/g or less.
<3>
The method for producing an aliphatic alcohol described in <1> or <2> in which the volume of pores with a pore size of 0.1 μm or more and 500 μm or less in the catalyst is, based on the total pore volume of the catalyst, preferably 55% or more, more preferably 60% or more, and further preferably 63% or more, and preferably 100% or less, more preferably 95% or less, further preferably 90% or less, furthermore preferably 85% or less, and furthermore preferably 84% or less.
<4>
The method for producing an aliphatic alcohol described in any one of <1> to <3> in which the mode of the pore size of the catalyst is preferably 0.035 μm or more, more preferably 0.1 μm or more, further preferably 15 μm or more, furthermore preferably 40 μm or more, furthermore preferably 50 μm or more, furthermore preferably 55 μm or more, and furthermore preferably 56 μm or more, and preferably 100 μm or less, more preferably 85 μm or less, further preferably 75 μm or less, furthermore preferably 70 μm or less, furthermore preferably 68 μm or less, and furthermore preferably 60 μm or less.
<5>
The method for producing an aliphatic alcohol described in any one of <1> to <4> in which the median of the pore size of the catalyst is preferably 0.1 μm or more, more preferably 1 μm or more, further preferably 8 μm or more, furthermore preferably 15 μm or more, furthermore preferably 20 μm or more, and furthermore preferably 25 μm or more, and preferably 100 μm or less, more preferably 85 μm or less, further preferably 70 μm or less, furthermore preferably 65 μm or less, furthermore preferably 60 μm or less, furthermore preferably 55 μm or less, furthermore preferably 50 μm or less, and furthermore preferably 49 μm or less.
<6>
The method for producing an aliphatic alcohol described in any one of <1> to <5> in which the porosity of the catalyst is preferably 30% or more, more preferably 35% or more, further preferably 40% or more, furthermore preferably 45% or more, and furthermore preferably 49% or more, and preferably 99% or less, more preferably 80% or less, further preferably 75% or less, furthermore preferably 70% or less, and furthermore preferably 67% or less.
<7>
The method for producing an aliphatic alcohol described in any one of <1> to <6> in which the specific surface area of the catalyst is preferably 0.1 m²/g or more, preferably 0.8 m²/g or more, more preferably 10 m²/g or more, further preferably 15 m²/g or more, furthermore preferably 20 m²/g or more, and furthermore preferably 21 m²/g or more, and preferably 500 m²/g or less, more preferably 400 m²/g or less, further preferably 250 m²/g or less, furthermore preferably 100 m²/g or less, furthermore preferably 60 m²/g or less, furthermore preferably 40 m²/g or less, furthermore preferably 35 m²/g or less, and furthermore preferably 32 m²/g or less.
<8>
The method for producing an aliphatic alcohol described in any one of <1> to <7> in which the bulk density of the catalyst is preferably 100 kg/m³ or more, more preferably 200 kg/m³ or more, further preferably 300 kg/m³ or more, furthermore preferably 400 kg/m³ or more, furthermore preferably 500 kg/m³ or more, furthermore preferably 600 kg/m³ or more, and furthermore preferably 680 kg/m³ or more, and preferably 10,000 kg/m³ or less, more preferably 2,500 kg/m³ or less, further preferably 2,000 kg/m³ or less, furthermore preferably 1,500 kg/m³ or less, furthermore preferably 1,000 kg/m³ or less, furthermore preferably 850 kg/m³ or less, and furthermore preferably 770 kg/m³ or less.

<9>

The method for producing an aliphatic alcohol described in any one of <1> to <8> in which the carried amount of the catalyst metal per unit mass of the catalyst is preferably 0.01 g/g or more, more preferably 0.3 g/g or more, and further preferably 0.33 g/g or more, and preferably 0.8 g/g or less, more preferably 0.6 g/g or less, further preferably 0.5 g/g or less, and furthermore preferably 0.4 g/g or less.

<10>

The method for producing an aliphatic alcohol described in any one of <1> to <9> in which the carried amount of the catalyst metal per unit volume of the catalyst is preferably 0.05 g/mL or more, more preferably 0.15 g/mL or more, further preferably 0.2 g/mL or more, furthermore preferably 0.25 g/mL or more, and furthermore preferably 0.3 g/mL or more, and preferably 1.0 g/mL or less, more preferably 0.8 g/mL or less, further preferably 0.6 g/mL or less, furthermore preferably 0.4 g/mL or less, furthermore preferably 0.35 g/mL or less, and furthermore preferably 0.3 g/mL or less.

<11>

The method for producing an aliphatic alcohol described in <1> in which the total pore volume of the catalyst is preferably 1.2 mL/g or more, and more preferably 1.8 mL/g or more, and preferably 10 mL/g or less, more preferably 2 mL/g or less, and further preferably 1.9 mL/g or less.

<12>

The method for producing an aliphatic alcohol described in <1> or <11> in which the volume of pores with a pore size of 0.1 μm or more and 500 μm or less in the catalyst is, based on the total pore volume of the catalyst, preferably 70% or more, more preferably 80% or more, further preferably 90% or more, and furthermore preferably 95% or more, and preferably 100% or less, more preferably 97% or less, and further preferably 96% or less.

<13>

The method for producing an aliphatic alcohol described in <1>, <11> or <12> in which the mode of the pore size of the catalyst is preferably 0.035 μm or more, more preferably 0.1 μm or more, further preferably 1 μm or more, furthermore preferably 10 μm or more, and furthermore preferably 12 μm or more, and preferably 100 μm or less, more preferably 40 μm or less, further preferably 30 μm or less, furthermore preferably 20 μm or less, and furthermore preferably 15 μm or less.

<14>

The method for producing an aliphatic alcohol described in any one of <1> and <11> to <13> in which the median of the pore size of the catalyst is preferably 0.1 μm or more, more preferably 1 μm or more, further preferably 8 μm or more, and furthermore preferably 10 μm or more, and preferably 100 μm or less, more preferably 40 μm or less, further preferably 30 μm or less, furthermore preferably 20 μm or less, furthermore preferably 15 μm or less, and furthermore preferably 11 μm or less.

<15>

The method for producing an aliphatic alcohol described in any one of <1> and <11> to <14> in which the porosity of the catalyst is preferably 30% or more, more preferably 60% or more, further preferably 75% or more, furthermore preferably 80% or more, and furthermore preferably 84% or more, and preferably 99% or less, more preferably 90% or less, and further preferably 85% or less.

<16>

The method for producing an aliphatic alcohol described in any one of <1> and <11> to <15> in which the specific surface area of the catalyst is preferably 0.1 m²/g or more, preferably 0.8 m²/g or more, more preferably 10 m²/g or more, and further preferably 14 m²/g or more, and preferably 500 m²/g or less, more preferably 400 m²/g or less, further preferably 250 m²/g or less, furthermore preferably 100 m²/g or less, furthermore preferably 60 m²/g or less, furthermore preferably 40 m²/g or less, furthermore preferably 35 m²/g or less, furthermore preferably 30 m²/g or less, furthermore preferably 20 m²/g or less, and furthermore preferably 15 m²/g or less.

<17>

The method for producing an aliphatic alcohol described in any one of <1> and <11> to <16> in which the bulk density of the catalyst is preferably 100 kg/m³ or more, more preferably 200 kg/m³ or more, further preferably 300 kg/m³ or more, furthermore preferably 400 kg/m³ or more, and furthermore preferably 450 kg/m³ or more, and preferably 10,000 kg/m³ or less, more preferably 2,500 kg/m³ or less, further preferably 2,000 kg/m³ or less, furthermore preferably 1,500 kg/m³ or less, furthermore preferably 1,000 kg/m³ or less, furthermore preferably 600 kg/m³ or less, and furthermore preferably 500 kg/m³ or less.

<18>

The method for producing an aliphatic alcohol described in any one of <1> and <11> to <17> in which the carried amount of the catalyst metal per unit mass of the catalyst is preferably 0.01 g/g or more, more preferably 0.1 g/g or more, further preferably 0.15 g/g or more, furthermore preferably 0.2 g/g or more, furthermore preferably 0.25 g/g or more, and furthermore preferably 0.27 g/g or more, and preferably 0.8 g/g or less, more preferably 0.35 g/g or less, and further preferably 0.3 g/g or less.

<19>

The method for producing an aliphatic alcohol described in any one of <1> and <11> to <18> in which the carried amount of the catalyst metal per unit volume of the catalyst is preferably 0.05 g/mL or more, more preferably 0.1 g/mL or more, and further preferably 0.12 g/mL or more, and preferably 1.0 g/mL or less, more preferably 0.2 g/mL or less, and further preferably 0.15 g/mL or less.

<20>

The method for producing an aliphatic alcohol described in any one of <1> to <19> in which the support of the catalyst has a porous structure.

<21>

The method for producing an aliphatic alcohol described in <20> in which the porous structure is made of preferably a metal, an alloy or ceramics, more preferably ceramics, further preferably silica, alumina, silica-alumina, calcia-magnesia-silica, titania or zirconia, further preferably silica, alumina, silica-alumina or calcia-magnesia-silica, and furthermore preferably silica-alumina or calcia-magnesia-silica.

<22>

The method for producing an aliphatic alcohol described in <20> or <21> in which the total pore volume of the porous structure is preferably 0.1 mL/g or more, more preferably 0.15 mL/g or more, further preferably 0.6 mL/g or more, furthermore preferably 0.9 mL/g or more, furthermore preferably 1 mL/g or more, furthermore preferably 1.1 mL/g or more, furthermore preferably 1.2 mL/g or more, furthermore preferably 2 mL/g or more, furthermore preferably 3 mL/g or more, and furthermore preferably 3.5 mL/g or more, and preferably 10 mL/g or less, furthermore preferably 7.5 mL/g or less, further preferably 7 mL/g or less, and furthermore preferably 5 mL/g or less.

<23>

The method for producing an aliphatic alcohol described in any one of <20> to <22> in which the volume of pores with a pore size of 0.1 μm or more and 500 μm or less in, the porous structure is, based on the total pore volume, preferably 50% or more, more preferably 80% or more, further preferably 90% or more, and furthermore preferably 95% or more, and preferably 100% or less.

<24>

The method for producing an aliphatic alcohol described in any one of <20> to <23> in which the mode of the pore size of the porous structure is preferably 0.1 μm or more, more preferably 1 μm or more, further preferably 10 μm or more, and furthermore preferably 20 μm or more, and preferably 500 μm or less, more preferably 200 μm or less, further preferably 100 μm or less, and furthermore preferably 60 μm or less.

<25>

The method for producing an aliphatic alcohol described in anyone of <20> to <24> in which the median of the pore size of the porous structure is preferably 0.1 μm or more, more preferably 1 μm or more, further preferably 10 μm or more, and furthermore preferably 20 μm or more, and preferably 500 μm or less, more preferably 200 μm or less, further preferably 140 μm or less, furthermore preferably 100 μm or less, and furthermore preferably 60 μm or less.

<26>

The method for producing an aliphatic alcohol described in any one of <20> to <25> in which the porosity of the porous structure is preferably 30% or more, more preferably 40% or more, further preferably 50% or more, furthermore preferably 55% or more, furthermore preferably 60% or more, and furthermore preferably 70% or more, and preferably 99% or less, more preferably 95% or less, and further preferably 93% or less.

<27>

The method for producing an aliphatic alcohol described in any one of <20> to <26> in which the bulk density of the porous structure is preferably 10 kg/m³ or more, more preferably 100 kg/m³ or more, and further preferably 150 kg/m³ or more, and preferably 7,000 kg/m³ or less, more preferably 4,000 kg/m³ or less, further preferably 2,400 kg/m³ or less, furthermore preferably 1,000 kg/m³ or less, furthermore preferably 500 kg/m³ or less, furthermore preferably 300 kg/m³ or less, and furthermore preferably 250 kg/m³ or less.

<28>

The method for producing an aliphatic alcohol described in any one of <20> to <27> in which the porous structure is preferably a fiber structure or a porous compact, and more preferably a fiber structure.

<29>

The method for producing an aliphatic alcohol described in any one of <20> to <28> in which the porous structure is a fiber structure, and the shape thereof is a sheet, a tube, a honeycomb or an indefinite shape, and preferably a sheet.

<30>

The method for producing an aliphatic alcohol described in any one of <20> to <29> in which the porous structure is a fiber structure, preferably woven fabric, knitted fabric or a nonwoven cloth, and more preferably a nonwoven cloth.

<31>

The method for producing an aliphatic alcohol described in any one of <1> to <30> in which the catalyst metal compound contained in the catalyst is an oxide.

<32>

The method for producing an aliphatic alcohol described in any one of <1> to <31> in which the catalyst is obtained by the following coating material preparation step, carrying step and calcining step:

the coating material preparation step: a step in which a catalyst precursor coating material or a catalyst metal oxide coating material is produced by dispersing a catalyst precursor or a catalyst metal oxide in a dispersion medium;

the carrying step: a step in which the catalyst precursor coating material or the catalyst metal oxide coating material obtained in the coating material preparation step is carried on the support; and the calcining step: a step in which the catalyst precursor or the catalyst metal oxide carried on the support in the carrying step is calcined.

<33>

The method for producing an aliphatic alcohol described in <32> in which the catalyst precursor is a compound which is converted to a catalyst metal oxide by calcining.

<34>

The method for producing an aliphatic alcohol described in <32> or <33> in which the carrying step is a carrying step by immersing the support in the catalyst precursor coating material or the catalyst metal oxide coating material.

<35>

The method for producing an aliphatic alcohol described in any one of <32> to <34> in which the catalyst precursor coating material or the catalyst metal oxide coating material contains a binder.

<36>

The method for producing an aliphatic alcohol described in <35> in which the binder is an oxide of a metal other than the catalyst metal.

<37>

The method for producing an aliphatic alcohol described in any one of <32> to <36> in which the concentration of the catalyst precursor or the catalyst metal oxide in the catalyst precursor coating material or the catalyst metal oxide coating material is preferably 1% by mass or more, more preferably 5% by mass or more, further preferably 15% by mass or more, and furthermore preferably 20% by mass or more, and preferably 40% by mass or less, and more preferably 35% by mass or less.

<38>

The method for producing an aliphatic alcohol described in any one of <1> to <37> in which the catalyst metal of the catalyst contains Co.

<39>
The method for producing an aliphatic alcohol described in any one of <1> to <37> in which the catalyst metal of the catalyst contains Cu.
<40>
The method for producing an aliphatic alcohol described in any one of <1> to <39> in which the catalyst contains a transition metal other than Co and Cu as a promoter component.
<41>
The method for producing an aliphatic alcohol described in <40> in which the promoter component is preferably one or more kinds selected from the group 3 metals, the group 4 metals, the group 5 metals, the group 6 metals, the group 10 metals, the group 12 metals, the group 13 metals and the group 14 metals, more preferably one or more kinds selected from Zr, Y, La, Ce, Si, Al, Sc, V, Nb, Mo, Pd, Pt, Ti, Cr, Zn, Ba, Fe, Al and Si, further preferably one or more kinds selected from Zr, Y, Mo, Pd, Ti, Zn and Ba, and furthermore preferably one or more elements selected from Zr, Y, Mo and Pd.
<42>
The method for producing an aliphatic alcohol described in <41> in which the total number of moles of the promoter metal based on 100 mol of Co or Cu is preferably 0.01 or more, more preferably 0.1 or more, further preferably one or more, and furthermore preferably three or more, and preferably 200 or less, more preferably 100 or less, further preferably 10 or less, and furthermore preferably six or less.
<43>
The method for producing an aliphatic alcohol described in <41> or <42> in which two or more kinds of promoter component are used, and the number of moles of the first promoter metal based on 100 mol of Co or Cu is preferably 0.001 or more, more preferably 0.01 or more, further preferably 0.1 or more, furthermore preferably one or more, and furthermore preferably 1.5 or more, and preferably 100 or less, more preferably 10 or less, and further preferably four or less.
<44>
The method for producing an aliphatic alcohol described in any one of <41> to <43> in which two or more kinds of promoter component are used, and the number of moles of the second promoter metal based on 100 mol of Co or Cu is preferably 0.0001 or more, more preferably 0.001 or more, further preferably 0.01 or more, furthermore preferably 0.1 or more, and furthermore preferably one or more, and preferably four or less, and more preferably two or less.
<45>
The method for producing an aliphatic alcohol described in <41> to <44> in which two or more kinds of promoter component are used, and the number of moles of the third promoter metal based on 100 mol of Co or Cu is preferably 0.0001 or more, more preferably 0.001 or more, further preferably 0.01 or more, and furthermore preferably 0.05 or more, and preferably one or less, more preferably 0.2 or less, and further preferably 0.1 or less.
<46>
The method for producing an aliphatic alcohol described in <40> in which the promoter component is preferably one or more kinds selected from Ti, Zn and Ba.
<47>
The method for producing an aliphatic alcohol described in <46> in which the total number of moles of the promoter metal based on 100 mol of Co or Cu is preferably 100 or more, and more preferably 110 or more, and preferably 200 or less, more preferably 150 or less, and further preferably 130 or less.
<48>
The method for producing an aliphatic alcohol described in <46> or <47> in which two or more kinds of promoter component are used, and the number of moles of the first promoter metal based on 100 mol of Co or Cu is preferably 100 or more, and more preferably 110 or more, and preferably 200 or less, more preferably 150 or less, and further preferably 130 or less.
<49>
The method for producing an aliphatic alcohol described in <46> to <48> in which two or more kinds of promoter component are used, and the number of moles of the second promoter metal based on 100 mol of Co or Cu is preferably 0.1 or more, more preferably one or more, and further preferably four or more, and preferably 10 or less, more preferably eight or less, and further preferably six or less.
<50>
The method for producing an aliphatic alcohol described in any one of <46> to <49> in which two or more kinds of promoter component are used, and the number of moles of the third promoter metal based on 100 mol of Co or Cu is preferably 0.1 or more, more preferably one or more, further preferably three or more, and furthermore preferably four or more, and preferably 10 or less, more preferably eight or less, further preferably six or less, and furthermore preferably five or less.
<51>
The method for producing an aliphatic alcohol described in any one of <1> to <50> in which the reaction temperature of the hydrogenation is preferably 150° C. or higher, more preferably 180° C. or higher, and further preferably 200° C. or higher, and preferably 300° C. or lower, more preferably 280° C. or lower, and further preferably 250° C. or lower.
<52>
The method for producing an aliphatic alcohol described in any one of <1> to <51> in which the reaction pressure of the hydrogenation is, as gauge pressure, preferably 1 MPa or higher, more preferably 5 MPa or higher, further preferably 10 MPa or higher, furthermore preferably 15 MPa or higher, and furthermore preferably 20 MPa or higher, and preferably 30 MPa or lower, and more preferably 27 MPa or lower.

EXAMPLES

The embodiments of the present invention are shown below.
1. Evaluation Methods
(1) Reactivity and Selectivity
(i) Analysis Method of Liquid Composition of Reaction Solution One drop of the reaction solution was put into a 10 mL sample bottle with a 2 mL disposable pipette, and 1 mL of trimethylsilylation (TMS) agent "TMSI-H" (manufactured by GL Sciences Inc.) was added thereto. The solution was heated at 40° C. for five minutes. The solution was diluted with 1.5 mL of hexane added thereto and filtered through a membrane filter with a pore size of 0.2 μm, and then the filtrate was analyzed by gas chromatography (GC).

In Examples 1 to 3 and Comparative Examples 1 and 2, with respect to lauric acid and dodecane in the reaction solution, the concentration (% by mass) was determined by multiplying the GC peak area percentage (%) by a factor based on dodecanol.

The factor was determined from the area ratio of a known amount of lauric acid "Lunac 2098" (manufactured by Kao Corporation) or a known amount of n-dodecane (manufactured by Wako Pure Chemical Industries, Ltd.) to a known amount of 1-dodecanol (manufactured by Wako Pure Chemical Industries, Ltd.).

In Example 4 and Comparative Example 3, with respect to palm kernel oil, the total of GC area percentages (%) derived from triglycerides obtained by GC measurement was regarded as the concentration (% by mass). With respect to alcohols, the total of GC area percentages (%) derived from respective alcohols having 8 to 18 carbon atoms was regarded as the concentration (% by mass). With respect to hydrocarbons, the total of GC area percentages (%) derived from respective hydrocarbons having 11 to 18 carbon atoms was regarded as the concentration (% by mass).

GC measurement condition (Examples 1 to 4 and Comparative Examples 1 to 3): "HP-6890" (manufactured by Hewlett-Packard Development Company, L.P.)

Capillary Column

"Ultra-AlloyUA+-1 (HT)" 15 m, thickness 0.15 µm, inside diameter 0.53 mm

Temperature 60° C. (two minutes)→10° C./min→350° C. (15 minutes)

Split ratio 15, Inj temperature 300° C., Det temperature 350° C.

In Examples 5 and 6 and Comparative Example 4, one drop of the reaction solution was put into a 10 mL sample bottle with a 2 mL disposable pipette and diluted with 1.5 mL of ethanol added thereto, and GC analysis was conducted. In Examples 5 and 6 and Comparative Example 4, the total of GC area percentages (%) derived from methyl esters obtained by GC measurement was regarded as the concentration (% by mass). With respect to alcohols, the total of GC area percentages (6) derived from respective alcohols having 8 to 18 carbon atoms was regarded as the concentration (% by mass). With respect to hydrocarbons, the total of GC area percentages (%) derived from respective hydrocarbons having 12 to 18 carbon atoms was regarded as the concentration (% by mass).

GC measurement condition (Examples 5 and 6 and Comparative Example 4): "HP-6890" (manufactured by Hewlett-Packard Development Company, L.P.)

Capillary Column

"HP-1" 30 m, thickness 0.25 µm, inside diameter 0.32 mm

Temperature 60° C. (0 minute)→8° C./min→300° C. (10 minutes)

Split ratio 9.1, Inj temperature 300° C., Det temperature 300° C.

(ii) Calculation Methods of Catalytic Activity and Selectivity (Examples 1 to 4 and Comparative Examples 1 to 3)

The catalytic activity was defined as follows with the decrease rate of the raw material and the 1 h reaction rate, with the point at which heating and pressurization were completed set as reaction time of 0 hour. The selectivity was defined with the hydrocarbon content (% by mass) at the alcohol content of 20% by mass.

Decrease rate of raw material=log{(fatty acid concentration of reaction solution at reaction time of 0 hour)/(fatty acid concentration of reaction solution at reaction time of 1 hour)}

Here, "log" represents the natural logarithm, and the same applies to the following descriptions.

1 h reaction rate [%]=100−(fatty acid concentration of reaction solution at reaction time of 1 hour)

Hydrocarbon content at alcohol content of 20% by mass=hydrocarbon content (% by mass) in reaction solution at alcohol content in reaction solution of 20% by mass/20(% by mass)

(iii) Calculation Methods of Catalytic Activity and Selectivity (Examples 5 and 6 and Comparative Example 4)

The catalytic activity was defined as follows with the decrease rate of the raw material and the 1 h reaction rate, with the point at which heating and pressurization were completed set as reaction time of 0 hour. The selectivity was defined with the hydrocarbon content (% by mass) at the alcohol content of 30% by mass.

Decrease rate of raw material=log{(methyl ester concentration of reaction solution at reaction time of 0.5 hours)/(methyl ester concentration of reaction solution at reaction time of 2 hours)}

1 h reaction rate [%]=100−(methyl ester concentration of reaction solution at reaction time of 1 hour)

Hydrocarbon content at alcohol content of 30% by mass=hydrocarbon content (% by mass) in reaction solution at alcohol content in reaction solution of 30% by mass/30(% by mass)

(iv) Measurement Method of Sulfur Concentration

The sulfur concentration was measured using low level sulfur analyzer "9000LLS" (manufactured by ANTEK Inc.) at a calcining temperature of 1,050° C. and with the voltage of the UV detector set at 840 V.

The sulfur concentration of palm kernel oil was measured after diluting 4.00 g of a sample with 5 mL of isooctane (manufactured by Kishida Chemical Co., Ltd.), and the sulfur concentration of a fatty acid methyl ester was measured without diluting the sample.

(2) Composition of Catalyst (i) Carried Amount of Catalyst Metal per Unit Mass

The carried amount of the catalyst metal per unit mass of the catalyst [g/g] was quantified using X-ray fluorescence analyzer "Rigaku ZSX100e" (manufactured by Rigaku Corporation).

(ii) Carried Amount of Catalyst Metal per Unit Volume

The carried amount of the catalyst metal per unit volume of the catalyst was calculated by the following equation.

Carried amount of catalyst metal per unit volume of catalyst [g/mL]=carried amount of catalyst metal per unit mass [g/g]×bulk density of catalyst [kg/m³]÷1,000

The bulk density of the catalyst was measured with the mercury porosimeter described in (4) (i) below.

(iii) Carried Amount of Catalyst Metal Oxide and Binder per Unit Mass

The carried amount of the catalyst metal oxide and the binder per unit mass of the catalyst was calculated by the following equation.

Carried amount of catalyst metal oxide and binder per unit mass [g/g]=(mass of catalyst after calcining [g]−mass of support before carrying step [g])/mass of catalyst [g]

(iv) Carried Amount of Catalyst Metal Oxide and Binder Per Unit Volume

Carried amount of catalyst metal oxide and binder per unit volume [g/mL]=carried mass of catalyst metal oxide and binder [g]÷volume of catalyst [mL]

The volume of the catalyst was calculated from the size of the catalyst measured using the ruler and calipers described in (5) below.

(3) Catalyst Metal Oxide Coating material

The particle size of the catalyst metal oxide particles in the catalyst metal oxide coating material was measured under the following condition using laser diffraction/scattering particle size distribution analyzer "LA-920" (manufactured by HORIBA, Ltd.).

Solvent: deionized water

Measurement condition: transmittance: 70 to 95%, stirring speed: level 2, refractive index: 1.16

(4) Pore Structure (i) Measurement Method of Pore Structure

The total pore volumes of the catalyst and the fiber structure, the volumes of pores with a pore diameter of 0.1 μm or more and 500 μm or less per unit mass, the modes of the pore sizes, the medians of the pore sizes, the porosities, the specific surface areas and the bulk densities were measured using mercury porosimeter "AutoPoreIV9500" (manufactured by Micromeritics Instrument Corporation). The pressure range for the measurement was 0.6 psia to 31,000 psia.

(ii) Percentage of Volume of Pores with Pore Diameter of 0.1 μm or More and 500 μm or Less in Total Pore Volume The percentage of the volume of pores with a pore diameter of 0.1 μm or more and 500 μm or less in the total pore volume was calculated by the following equation.

Percentage of volume of pores with pore diameter of 0.1 μm or more and 500 μm or less in total pore volume=volume of pores with pore diameter of 0.1 μm or more and 500 μm or less [mL/g]÷total pore volume [mL/g]×100[%]

(5) External Sizes (i) Thicknesses of Fiber Structure and Catalyst Fiber Structure The thickness of the fiber structure was measured using constant-pressure thickness gauge "PG-11" (manufactured by Teclock Corporation) with a constant-pressure load of 0.363 N at pressure of 0.363 kPa.

(ii) Measurement Method of External Sizes of Fiber Structure and Catalyst Fiber Structure Except for Thicknesses The external sizes of the catalyst and the porous structure other than the thicknesses were measured using a ruler and calipers.

2. Production Examples of Catalyst Metal Oxide

Catalyst Metal Oxide a (Co—Y—Pd—Mo)

An aqueous mixture solution of cobalt nitrate (manufactured by Wako Pure Chemical Industries, Ltd.), yttrium nitrate (n-hydrate) (manufactured by Sigma-Aldrich Co. LLC.) and palladium nitrate (manufactured by Wako Pure Chemical Industries, Ltd.) with an atomic ratio Co:Y:Pd of 100:5:0.08 and an aqueous solution of ammonium carbonate (manufactured by Wako Pure Chemical Industries, Ltd.) were stirred and mixed at room temperature. The generated precipitate was thoroughly washed with water and then dried at 110° C. After drying, an aqueous solution of ammonium molybdate (manufactured by Wako Pure Chemical Industries, Ltd.) was mixed therewith and stirred at an atomic ratio Co:Mo of 100:1 at room temperature, followed by evaporation and drying with an evaporator. Then, the mixture was calcined at 600° C. for four hours, and a catalyst metal oxide a (Co—Y—Pd—Mo oxide) was obtained. The atomic ratio of the obtained catalyst metal oxide a was Co/Y/Pd/Mo=100/3.9/0.08/1.5.

Catalyst Metal Oxide b (Co—Zr—Mo)

A catalyst metal oxide b (Co—Zr—Mo oxide) was obtained in the same manner as in the preparation example of the catalyst metal oxide a, except that, in the preparation of the catalyst precursor, an aqueous mixture solution of cobalt nitrate (manufactured by Wako Pure Chemical Industries, Ltd.) and zirconium oxynitrate (manufactured by Wako Pure Chemical Industries, Ltd.) with an atomic ratio Co:zirconium of 100:5 was used. The atomic ratio of the obtained catalyst metal oxide b was Co/Zr/Mo=100/1.8/1.4.

Catalyst Precursor c (Cu—Zn—Ti—Ba)

First, in accordance with the method described in Example 5 of JP-A-5-177140, a catalyst precursor c containing CuO, ZnO and BaO carried on $TiO_2$ was obtained. The generated precipitate was thoroughly washed with water, and then the solid component was dried in air atmosphere at atmospheric pressure at 110° C. The atomic ratio of the obtained catalyst precursor c was Cu/Zn/Ti/Ba=100/5.0/112.3/4.8.

Catalyst Precursor d (Ni—Si—Mg)

Into a 2 L separable flask, 800 g of deionized water and 232 g of nickel nitrate hexahydrate (manufactured by Wako Pure Chemical Industries, Ltd.) were fed, and the mixture was heated to 80° C. while stirring the mixture. The total amount of a solution which had been prepared by dissolving 33 g of water glass of JIS No. 3 (manufactured by Kishida Chemical Co., Ltd.) and 113 g of sodium carbonate (manufactured by Wako Pure Chemical Industries, Ltd.) in 630 g of deionized water and which had been heated to 80° C. was added thereto, while stirring the mixture. After the addition, 24 g of magnesium nitrate hexahydrate (manufactured by Wako Pure Chemical Industries, Ltd.) was added, and the generated slurry was stirred at 80° C. for an hour. Then, the solid component was separated from the slurry by filtration. The obtained solid component was thoroughly washed with water and then dried in air atmosphere at atmospheric pressure at 110° C. The atomic ratio of a catalyst precursor d, which was calculated from the amounts of the raw materials, was Mg/Ni=1/8.5.

3. Production Examples of Catalyst (1) Porous Structures

The porous structures used as the supports in the Production Examples of the catalyst of the present invention are as follows. The physical properties are shown in Table 1.

Calcia-magnesia-silica fiber sheet: "Superwool 607" (manufactured by Shin-Nippon Thermal Ceramics. Corporation)

Silica-alumina fiber sheet: "MC Paper" (manufactured by Nippon Sheet Glass Co. Ltd.)

TABLE 1

| | Calcia-magnesia-silica fiber sheet | Silica-alumina fiber sheet |
|---|---|---|
| Bulk density [kg/m$^3$] | 199 | 208 |
| Mode of pore size [μm] | 52.0 | 22.7 |
| Median of pore size [μm] | 58.3 | 23.3 |
| Total pore volume [mL/g] | 3.60 | 4.43 |
| Porosity [%] | 71.9 | 92.1 |
| Percentage of volume of pores with pore diameter of 0.1-500 μm in total pore volume [%] | 100.0 | 97.1 |

(2) Binders

The binder sol or the binders used in the Production Examples and the Comparative Production Examples of the catalyst are as follows.

Zirconia sol: "ZR-30BS" (manufactured by Nissan Chemical Industries, Ltd., solid concentration: 30% by mass)

Zirconia: "RC-100" (manufactured by Daiichi Kigenso Kagaku Kogyo Co., Ltd.)

Titania sol: "AM-15" (manufactured by Taki Chemical Co., Ltd., solid concentration: 16.6% by mass)

Silica sol: "Snowtex ST-20" (manufactured by Nissan Chemical Industries, Ltd., solid concentration: 20% by mass)

(3) Production Examples 1 to 5 of Catalyst

Catalyst 1 (Co—Y—Pd—Mo)

A catalyst containing a catalyst metal carried on a fiber structure was produced according to the following steps.

(i) Coating Material Preparation Step

In a 250 mL plastic container, 48.0 g of the catalyst metal oxide a, 40 g of the zirconia sol as the binder, 53 g of deionized water and 9 g of 2-propanol (manufactured by Kanto Chemical Co., Inc.) as the solvents and 160 g of titania beads with a diameter of 1.0 mm were enclosed, and the mixture was treated using a disperser for test (JIS K5101-1-2, manufactured by Toyo Seiki Seisaku-sho, Ltd.) according to the method described in JIS K501-1-2 for 30 minutes, thereby obtaining a catalyst metal oxide coating material x with a solid content of 40% by mass. The ratio by mass of the solid component of the catalyst metal oxide to the solid component of the binder was 80/20.

(ii) Carrying Step

A Petri dish (φ 86 mm, height 14 mm) was filled with the catalyst metal oxide coating material x obtained in the coating material preparation step, and the calcia-magnesia-silica fiber sheet (20 mm×5 mm, thickness 1.0 mm) was immersed therein, turned over after 150 seconds and further immersed for 150 seconds, that is, the sheet was immersed for 300 seconds in total.

The immersed fiber structure was dried on a stainless plate coated with polytetrafluoroethylene (230 mm×230 mm, thickness 1.5 mm) in air atmosphere at atmospheric pressure at 120° C. for 60 minutes.

(iii) Calcining Step

The dried fiber structure was calcined in air atmosphere at atmospheric pressure at 600° C. for two hours, and a catalyst 1 was thus obtained.

Catalyst 2 (Co—Y—Pd—Mo)

A catalyst 2 was obtained in the same manner as the catalyst 1, except that the coating material preparation step (i) was conducted as follows, that a shaping step was conducted as follows after the carrying step (ii) and before the calcining step (iii) and that the silica-alumina fiber sheet (50 mm×50 mm, thickness 1.0 mm) was used as the fiber structure.

(i) Coating Material Preparation Step

In a 50 mL plastic container, 9.8 g of the catalyst metal oxide a, 8.2 g of the zirconia sol and 17.0 g of deionized water were enclosed, and the mixture was preliminarily mixed by shaking the container until blocks of powder disappeared.

Next, using thin-film spin system high-speed mixer "Filmix type 40-40" (manufactured by Primix Corporation), the preliminarily mixed materials were treated at a peripheral speed of 30 m/s for 30 seconds, and a catalyst metal oxide coating material y in a slurry state with a solid content of 35% by mass was obtained. The ratio by mass of the solid component of the catalyst metal oxide to the solid component of the binder was 80/20. The particle size distribution of the catalyst metal oxide coating material y was measured by laser diffractometry, and the mode of the particle size of the catalyst metal oxide particles in the catalyst metal oxide coating material y was 1.54 µm.

Shaping Step

The fiber structure was dried by the same carrying step as that of the catalyst 1, except that the catalyst metal oxide coating material y was used instead of the catalyst metal oxide coating material x. Then, the fiber structure (50 mm×50 mm×1.0 mm) was cut using a Thomson blade in such a manner that an area of 40 mm×40 mm of the fiber structure was cut into 16 pieces each having a size of 20 mm×5 mm.

Catalyst 3 (Co—Zr—Mo)

A catalyst 3 was obtained in the same manner as in the Production Example of the catalyst 2, except that the calcia-magnesia-silica fiber sheet (20 mm×5 mm, thickness 1.0 mm) was used as the fiber structure, that a catalyst metal oxide coating material z was obtained in the coating material preparation step using 8.4 g of the catalyst metal oxide b (Co—Zr—Mo), 7.0 g of the binder and 19.6 g of deionized water and that the shaping step was not conducted.

In this regard, the solid content of the catalyst metal oxide coating material z obtained in the coating material preparation step was 30% by mass, and the ratio by mass of the solid component of the catalyst metal oxide to the solid component of the binder was 4/1. The mode of the particle size of the catalyst metal oxide particles in the catalyst metal oxide coating material z was 1.10 µm.

Catalyst 4 (Cu—Zn—Ti—Ba)

A catalyst 4 was obtained in the same manner as the catalyst 2, except that the coating material preparation step (i) and the calcining step (iii) were conducted as follows, that the silica-alumina fiber sheet (20 mm×5 mm, thickness 1.0 mm) was used as the fiber structure and that the shaping step was not conducted.

(i) Coating Material Preparation Step

In a 50 mL plastic container, 6.0 g of the catalyst precursor c, 9.0 g of the titania sol as the binder and 15.0 g of deionized water as the solvent were enclosed, and the mixture was preliminarily mixed by shaking the container until blocks of powder disappeared.

Next, using thin-film spin system high-speed mixer "Filmix type 40-40" (manufactured by Primix Corporation), the preliminarily mixed materials were treated at a peripheral speed of 30 m/s for 30 seconds, and a catalyst precursor coating material w in a slurry state with a solid content of 25% by mass was obtained. The ratio by mass of the solid component of the catalyst precursor to the solid component of the binder was 80/20. The particle size distribution of the catalyst precursor coating material w was measured by laser diffractometry, and the mode of the particle size of the catalyst precursor particles in the catalyst precursor coating material w was 1.8 µm.

(iii) Calcining Step

The fiber structure carrying the obtained catalyst precursor coating material w was calcined in air atmosphere at atmospheric pressure at 400° C. for five hours, and a catalyst 4 was thus obtained.

Catalyst 5 (Ni—Si—Mg)

(i) Coating Material Preparation Step

In a 250 mL plastic container, 36 g of the catalyst precursor d, 45 g of the silica sol, 58.5 g of deionized water, 10.5 g of isopropyl alcohol (manufactured by Kanto Chemical Co., Inc.) and 160 g of titania beads with a diameter of 0.8 mm were enclosed, and the mixture was treated using a disperser for test (JIS K5101-1-2, manufactured by Toyo Seiki Seisaku-sho, Ltd.) according to the method described in JIS K501-1-2 for 30 minutes, thereby obtaining a catalyst precursor coating material v with a solid concentration of 30% by mass. The ratio by mass of the solid component of the catalyst precursor d to the solid component of the binder was 80/20. The mode of the particle size of the catalyst precursor in the catalyst precursor coating material v was 1 µm.

(ii) Carrying Step

A Petri dish (φ86 mm, height 14 mm) was filled with the catalyst precursor coating material v with a solid content of 30% by mass obtained in the coating material preparation step, and the calcia-magnesia-silica fiber sheet (10 mm×2.5 mm, thickness 1.0 mm) was immersed therein, turned over after 150 seconds and further immersed for 150 seconds, that is, the sheet was immersed for 300 seconds in total. The immersed fiber structure was dried on a stainless gauze with a sieve opening of 1 mm of in air atmosphere at atmospheric pressure at 130° C. for 30 minutes.

(iii) Calcining Step

The fiber structure carrying the catalyst precursor coating material obtained in the carrying step was calcined in air atmosphere at atmospheric pressure at 400° C. for two hours, and a catalyst 5 was obtained.

4. Comparative Production Examples of Catalyst

Catalyst 6 (Co—Y—Pd—Mo)

A catalyst 6 was obtained by mixing 148 g of the catalyst metal oxide a with 112 g of zirconia "RC-100" (manufactured by Daiichi Kigenso Kagaku Kogyo Co., Ltd.), molding the mixture into a noodle shape by extrusion molding using the zirconia sol (solid content 30 g) as the binder and then calcining the molded product in air atmosphere at atmospheric pressure at 400° C. for two hours.

Catalyst 7 (Co—Zr—Mo)

A catalyst 7 was obtained in the same manner as in the Production Example of the catalyst 6, except that the catalyst metal oxide b was used in the extrusion molding step.

Catalyst 8 (Cu—Zn—Ti—Ba)

A catalyst 8 was obtained by tablet-compressing the catalyst precursor c into a cylinder form and calcining the tablet-compressed product in air atmosphere at atmospheric pressure at 400° C. for two hours.

The physical properties of the catalysts 1 to 8 obtained in the Production Examples and the Comparative Production Examples are summarized in Tables 2 to 4 below.

TABLE 2

| Catalyst | 1 | 2 | 3 | 6 | 7 |
|---|---|---|---|---|---|
| Metal | Co—Y—Pd—Mo | Co—Y—Pd—Mo | Co—Zr—Mo | Co—Y—Pd—Mo | Co—Zr—Mo |
| Molding method | Carried on inorganic fiber support | Carried on inorganic fiber support | Carried on inorganic fiber support | Extrusion molded product | Extrusion molded product |
| Carried amount of catalyst metal per unit volume [g/mL] | 0.35 | 0.25 | 0.25 | 0.31 | 0.21 |
| Carried amount of catalyst metal per unit mass [g/g] | 0.45 | 0.33 | 0.37 | 0.14 | 0.15 |
| Carried amount of catalyst metal oxide and binder per unit volume [g/mL] | 0.68 | 0.60 | 0.52 | — | — |
| Percentage of volume of pores with pore diameter of 0.1-500 µm in total pore volume [%] | 63.5 | 63.7 | 83.1 | 1.5 | 4.2 |
| Mode of pore size [µm] | 68 | 0.038 | 56 | 0.015 | 0.034 |
| Median of pore size [µm] | 27.5 | 8.37 | 48.2 | 0.02 | 0.03 |
| Total pore volume [mL/g] | 0.55 | 0.63 | 0.95 | 0.25 | 0.36 |
| Porosity [%] | 42.8 | 49.0 | 67.0 | 53.9 | 50.2 |
| Specific surface area [m$^2$/g] | 20.5 | 21.6 | 31.5 | 77.0 | 50.2 |
| Bulk density [kg/m$^3$] | 765.4 | 769.2 | 680.9 | 2198.0 | 1490.5 |
| Number of moles of Y/100 mol of Co | 3.9 | 5.3 | — | 5.6 | — |
| Number of moles of Pd/100 mol of Co | 0.08 | 0.1 | — | 0.2 | — |
| Number of moles of Mo/100 mol of Co | 1.5 | 0.8 | 1.4 | 1.6 | 1.4 |
| Number of moles of Zr/100 mol of Co | — | — | 1.8 | — | 1.8 |

TABLE 3

| Catalyst | 4 | 8 |
|---|---|---|
| Metal | Cu—Zn—Ti—Ba | Cu—Zn—Ti—Ba |
| Molding method | Carried on inorganic fiber support | Tablet-compressed product |
| Carried amount of catalyst metal per unit volume [g/mL] | 0.12 | 0.61 |
| Carried amount of catalyst metal per unit mass [g/g] | 0.27 | 0.35 |
| Carried amount of catalyst metal oxide and binder per unit volume [g/mL] | 1.0 | — |
| Percentage of volume of pores with pore diameter of 0.1-500 µm in total pore volume [%] | 95.9 | 2.1 |
| Mode of pore size [µm] | 12.1 | 0.012 |
| Median of pore size [µm] | 10.0 | 0.020 |
| Total pore volume [mL/g] | 1.86 | 0.23 |
| Porosity [%] | 84.3 | 38.8 |
| Specific surface area [m$^2$/g] | 14.8 | 56.3 |
| Bulk density [kg/m$^3$] | 452.2 | 1726.1 |

TABLE 3-continued

| | | |
|---|---|---|
| Number of moles of Zn/100 mol of Cu | 5.2 | 5.0 |
| Number of moles of Ti/100 mol of Cu | 167.0 | 112.3 |
| Number of moles of Ba/100 mol of Cu | 4.6 | 4.8 |

TABLE 4

| | |
|---|---|
| Catalyst | 5 |
| Metal | Ni—Si—Mg |
| Molding method | Carried on inorganic fiber support |
| Carried amount of catalyst metal per unit volume [g/mL] | 0.191 |
| Carried amount of catalyst metal per unit mass [g/g] | 0.25 |
| Carried amount of catalyst metal oxide and binder per unit volume [g/mL] | 0.391 |
| Percentage of volume of pores with pore diameter of 0.1-500 μm in total pore volume [%] | 83.9 |
| Mode of pore size [μm] | 52.0 |
| Median of pore size [μm] | 33.7 |
| Total pore volume [mL/g] | 0.916 |
| Porosity [%] | 69.9 |
| Specific surface area [m$^2$/g] | 37.2 |
| Bulk density [kg/m$^3$] | 764 |

(ii) Hydrogenation

A 500 mL autoclave was filled with the catalyst 1 and 200 g of lauric acid "Lunac L-98" (manufactured by Kao Corporation) in such a manner that the Co concentration became 0.65% by mass based on lauric acid, and the atmosphere in the autoclave was replaced with hydrogen. Then, hydrogenation of lauric acid was conducted by batch process. The reaction condition was 24.5 MPa (gauge pressure), 230° C., a stirring speed of 900 rpm and a hydrogen flow rate of 5 NL/min. The reaction was conducted with the point at which heating and pressurization were completed set as reaction time of 0 hour. During the reaction, samples were taken from the reaction solution, and the liquid composition was analyzed. The results are shown in Table 5.

Examples 2 and 3 and Comparative Examples 1 and 2

Reduction and hydrogenation were conducted in the same manner as in Example 1, except that the respective catalysts shown in Table 2 were used. The results are shown in Table 5.

TABLE 5

| | Example 1 | Example 2 | Comparative Example 1 | Example 3 | Comparative Example 2 |
|---|---|---|---|---|---|
| Catalyst | 1 | 2 | 6 | 3 | 7 |
| Metal | Co—Y—Pd—Mo | Co—Y—Pd—Mo | Co—Y—Pd—Mo | Co—Zr—Mo | Co—Zr—Mo |
| Total pore volume [mL/g] | 0.55 | 0.63 | 0.25 | 0.95 | 0.36 |
| Percentage of volume of pores with pore diameter of 0.1-500 μm in total pore volume [%] | 63.5 | 63.7 | 1.5 | 83.1 | 4.2 |
| Raw material | Lauric acid | Lauric acid | Lauric acid | Lauric acid | Lauric acid |
| Mass % of Co based on lauric acid | 0.65% | 0.65% | 0.65% | 0.65% | 0.65% |
| Reaction temperature [° C.] | 230 | 230 | 230 | 230 | 230 |
| Reaction pressure (gauge pressure) [MPa] | 24.5 | 24.5 | 24.5 | 24.5 | 24.5 |
| Hydrogen flow rate [L/min.] | 5 | 5 | 5 | 5 | 5 |
| Hydrogen flow rate [H$_2$ mol/lauric acid mol] | 13.4 | 13.4 | 13.4 | 13.4 | 13.4 |
| Decrease rate of raw material | 2.55 | 1.12 | 0.84 | 1.68 | 0.35 |
| Reaction rate (%) at 1 h | 92.6 | 71.8 | 57.6 | 83.3 | 33.3 |
| Hydrocarbon content (mass %) at alcohol content of 20 mass % | 0.1 | 0.04 | 0.18 | 0.13 | 0.24 |

Example 1

(i) Reduction

The catalyst 1 was put on a plate for calcining and placed in an electric furnace capable of generating a reducing atmosphere. Hydrogen diluted to 4% by volume with nitrogen was allowed to flow, and the temperature was raised to 500° C. at atmospheric pressure. Reduction was conducted until the absorption of hydrogen stopped. The period of the reduction was five hours. Next, the system was purged with nitrogen and cooled to room temperature at the same time. Then, in order to oxidize and stabilize the surface of the reduced catalyst, air diluted with nitrogen (oxygen concentration [1% by volume]) was allowed to flow for seven hours.

Example 4

The catalyst 1 was reduced under the same condition as in Example 1. Next, a 500 mL autoclave was filled with the catalyst 1, water and 150 g of refined palm kernel oil in such a manner that the Co concentration became 1.3% by mass based on the refined palm kernel oil and the number of moles of water became 20 times the number of moles of the refined palm kernel oil, and the atmosphere in the autoclave was replaced with hydrogen. Then, hydrogenation of the refined palm kernel oil was conducted by batch process. The reaction condition was 24.5 MPa (gauge pressure), 230° C., a stirring speed of 900 rpm, in a hydrogen atmosphere and a sealed system. The reaction was conducted with the point at which heating and pressurization were completed set as reaction time of 0 hour. During the reaction, samples were taken from the reaction solution, and the liquid composition was analyzed. The results are shown in Table 6.

Comparative Example 3

Reduction and hydrogenation were conducted in the same manner as in Example 4, except that the catalyst was replaced with the catalyst 6 as shown in Table 6. The results are shown in Table 6.

TABLE 6

|  | Example 4 | Comparative Example 3 |
| --- | --- | --- |
| Catalyst | 1 | 6 |
| Metal | Co—Y—Pd—Mo | Co—Y—Pd—Mo |
| Total pore volume [mL/g] | 0.55 | 0.25 |
| Percentage of volume of pores with pore diameter of 0.1-500 μm in total pore volume [%] | 63.5 | 1.5 |
| Raw material | Palm kernel oil | Palm kernel oil |
| Mass % of Co based on palm kernel oil | 1.30% | 1.30% |
| Reaction temperature [° C.] | 230 | 230 |
| Reaction pressure (gauge pressure) [MPa] | 24.5 | 24.5 |
| Amount of added $H_2O$ [$H_2O$-mol/PKO-mol] | 20 | 20 |
| Decrease rate of raw material | 1.39 | 0.83 |
| Reaction rate (%) at 1 h | 75.5 | 67.7 |
| Hydrocarbon content (mass %) at alcohol content of 20 mass % | 0.005 | 0.08 |

Example 5

(i) Reduction

A 500 mL autoclave was filled with the catalyst 4 and 200 g of lauryl alcohol "Kalcol 2098" (manufactured by Kao Corporation) in such a manner that the Cu concentration became 0.65% by mass based on lauryl alcohol, and the atmosphere in the autoclave was replaced with hydrogen. Then, the catalyst was reduced by batch process. The reaction condition was 1.0 MPa (gauge pressure), 200° C., a stirring speed of 900 rpm and a hydrogen flow rate of 5 NL/min. The reduction was conducted for two hours with the point at which heating and pressurization were completed set as reaction time of 0 hour.

(ii) Hydrogenation

A 500 mL autoclave was filled with the reduced catalyst 4 and 200 g of a methyl ester derived from palm kernel oil (manufactured by Kao Corporation) in such a manner that the Cu concentration became 0.65% by mass based on the methyl ester, and the atmosphere in the autoclave was replaced with hydrogen. Then, hydrogenation of the methyl ester was conducted by batch process. The reaction condition was 22.5 MPa (gauge pressure), 250° C., a stirring speed of 900 rpm and a hydrogen flow rate of 5 NL/min. The reaction was conducted with the point at which heating and pressurization were completed set as reaction time of 0 hour. During the reaction, samples were taken from the reaction solution, and the liquid composition was analyzed. The results are shown in Table 7.

Comparative Example 4

Reduction and hydrogenation were conducted in the same manner as in Example 5, except that the catalyst was replaced with the catalyst 8 as shown in Table 7. The results are shown in Table 7.

Example 6

Desulfurization of Methyl Ester (i) Reduction of Catalyst

The catalyst 5 was reduced in a gas phase at 450° C. at atmospheric pressure in a hydrogen atmosphere of 4% by volume for five hours and then stabilized at 25° C. at atmospheric pressure in an oxygen atmosphere of 1% by volume for eight hours.

A 500 mL autoclave was filled with 0.154 g of the stabilized catalyst 5 and 240 g of lauryl alcohol, and the atmosphere in the autoclave was replaced with hydrogen. Then, the catalyst was reduced in a liquid phase by batch process. The reaction condition was 1.0 MPa (gauge pressure), 200° C., a stirring speed of 900 rpm and a hydrogen flow rate of 5 NL/min. The reduction was conducted for two hours with the point at which heating and pressurization were completed set as reaction time of 0 hour.

(ii) Desulfurization

A 500 mL autoclave was filled with the total amount of the catalyst 5 which had been reduced in a gas phase and reduced in a liquid phase and 240 g of a methyl ester derived from palm kernel oil containing 0.47 mg/kg of sulfur components as impurities (manufactured by Kao Corporation), and the atmosphere in the autoclave was replaced with hydrogen. Then, desulfurization of the methyl ester was conducted by batch process. The reaction condition was 24.5 MPa (gauge pressure), 135° C., a stirring speed of 900 rpm and a hydrogen flow rate of 5 NL/min. The reaction was conducted with the point at which heating and pressurization were completed set as reaction time of 0 hour. During the reaction, samples were taken from the reaction solution, and the sulfur content was analyzed. As a result of the analysis of the reaction solution after two hours of reaction, the sulfur content in the methyl ester was 0.21 mg/kg.

Alcohol Production (i) Reduction

Reduction was conducted under the same condition as in (i) Reduction in Example 5, except that a 500 mL autoclave was filled with the catalyst 4 in such a manner that the Cu concentration became 0.81% by mass based on lauryl alcohol.

(ii) Hydrogenation

Hydrogenation, sampling of the reaction solution and analysis of the liquid composition were conducted under the same conditions as in (ii) Hydrogenation in Example 5, except that a 500 mL autoclave was filled with the methyl ester obtained through the desulfurization as the methyl ester. The results are shown in Table 7.

TABLE 7

|  | Example 5 | Example 6 | Comparative Example 4 |
|---|---|---|---|
| Catalyst | 4 | 4 | 8 |
| Metal | Cu—Zn—Ti—Ba | Cu—Zn—Ti—Ba | Cu—Zn—Ti—Ba |
| Total pore volume [mL/g] | 1.86 | 1.86 | 0.23 |
| Percentage of volume of pores with pore diameter of 0.1-500 μm in total pore volume [%] | 95.9 | 95.9 | 2.1 |
| Raw material | Methyl ester derived from palm kernel oil | Methyl ester derived from palm kernel oil | Methyl ester derived from palm kernel oil |
| Mass % of Cu based on methyl ester | 0.65% | 0.65% | 0.65% |
| Reaction temperature [° C.] | 250 | 250 | 250 |
| Reaction pressure (gauge pressure) [MPa] | 22.5 | 22.5 | 22.5 |
| Hydrogen flow rate [L/min.] | 5 | 5 | 5 |
| Hydrogen flow rate [$H_2$ mol/methyl ester mol] | 15.4 | 19.3 | 15.4 |
| Decrease rate of raw material | 1.07 | 1.10 | 0.32 |
| Reaction rate (%) at 1 h | 71.2 | 63.7 | 33.2 |
| Hydrocarbon content (mass %) at alcohol content of 30 mass % | 0.07 | 0.06 | 0.16 |

The invention claimed is:

1. A method for producing an aliphatic alcohol having 8 or more and 22 or less carbon atoms through hydrogenation of a fatty acid or a fatty acid ester using a catalyst, wherein the catalyst carries a catalyst metal on a support,
(a) the catalyst contains one or more elements selected from Co and Cu as the catalyst metal,
(b) the total pore volume of the catalyst is 0.05 mL/g or more, and
(c) the volume of pores with a pore size of 0.1 μm or more and 500 μm or less is 50% or more of the total pore volume of the catalyst, and
wherein the median of the pore size of the catalyst is 1 μm or more and 100 μm or less.

2. The method for producing an aliphatic alcohol according to claim 1, wherein the porosity of the catalyst is 30% or more and 99% or less.

3. The method for producing an aliphatic alcohol according to claim 1, wherein the reaction temperature of the hydrogenation is 150° C. or higher and 300° C. or lower.

4. The method for producing an aliphatic alcohol according to claim 1, wherein the reaction pressure of the hydrogenation is 1 MPa or higher and 30 MPa or lower as gauge pressure.

5. The method for producing an aliphatic alcohol according to claim 1, wherein the catalyst is reduced before the hydrogenation.

6. The method for producing an aliphatic alcohol according to claim 1, wherein the carried amount of the catalyst metal per unit volume of the catalyst is 0.05 g/mL or more and 1.0 g/mL or less.

7. The method for producing an aliphatic alcohol according to claim 1, wherein the carried amount of the catalyst metal per unit mass of the catalyst is 0.01 g/g or more and 0.8 g/g or less.

8. The method for producing an aliphatic alcohol according to claim 1, wherein the support has a porous structure.

9. The method for producing an aliphatic alcohol according to claim 1, wherein the support has a fiber structure.

10. The method for producing an aliphatic alcohol according to claim 1, wherein the catalyst is obtained by the following coating material preparation step, carrying step and calcining step:
the coating material preparation step: a step in which a catalyst precursor coating material or a catalyst metal oxide coating material is produced by dispersing a catalyst precursor or a catalyst metal oxide in a dispersion medium;
the carrying step: a step in which the catalyst precursor coating material or the catalyst metal oxide coating material obtained in the coating material preparation step is carried on the support; and
the calcining step: a step in which the catalyst precursor or the catalyst metal oxide carried on the support in the carrying step is calcined.

11. The method for producing an aliphatic alcohol according to claim 10, wherein the catalyst precursor is a compound which is converted to a catalyst metal oxide by calcining.

12. The method for producing an aliphatic alcohol according to claim 10, wherein the carrying step is a carrying step by immersing the support in the catalyst precursor coating material or the catalyst metal oxide coating material.

13. The method for producing an aliphatic alcohol according to claim 10, wherein the catalyst precursor coating material or the catalyst metal oxide coating material contains a binder.

14. The method for producing an aliphatic alcohol according to claim 13, wherein the binder is an oxide of a metal other than the catalyst metal.

15. The method for producing an aliphatic alcohol according to claim 1, wherein the catalyst contains a transition metal other than Co and Cu as a promoter component.

16. The method for producing an aliphatic alcohol according to claim 15, wherein the total number of moles of the promoter metal is 0.01 or more and 200 or less based on 100 mol of the Co or the Cu.

17. The method for producing an aliphatic alcohol according to claim 15, wherein two or more kinds of promoter component are used, and the number of moles of a first promoter metal is 0.001 or more and 100 or less based on 100 mol of the Co or the Cu.

18. The method for producing an aliphatic alcohol according to claim 15, wherein two or more kinds of promoter component are used, and the number of moles of a second promoter metal is 0.0001 or more and 4 or less based on 100 mol of the Co or the Cu.

19. The method for producing an aliphatic alcohol according to claim 15, wherein two or more kinds of promoter component are used, and the number of moles of a third promoter metal is 0.0001 or more and 1 or less based on 100 mol of the Co or the Cu.

* * * * *